(12) United States Patent
Moinet et al.

(10) Patent No.: US 7,375,130 B2
(45) Date of Patent: May 20, 2008

(54) ANTIDIABETIC COMPOUNDS COMPRISING BENZOFURAN AND BENZOTHIOPHENE DERIVATIVES

(75) Inventors: Gérard Moinet, Orsay (FR); Caroline Leriche, Paris (FR); Micheline Kergoat, Bures-sur-Yvette (FR)

(73) Assignee: Merck Patent Gesellschaft mit beschrankter Haftung, Darmstadt (DE)

( * ) Notice: Subject to any disclaimer, the term of this patent is extended or adjusted under 35 U.S.C. 154(b) by 0 days.

(21) Appl. No.: 10/580,033

(22) PCT Filed: Oct. 26, 2004

(86) PCT No.: PCT/EP2004/012075

§ 371 (c)(1),
(2), (4) Date: May 19, 2006

(87) PCT Pub. No.: WO2005/054225

PCT Pub. Date: Jun. 16, 2005

(65) Prior Publication Data

US 2007/0078178 A1    Apr. 5, 2007

(30) Foreign Application Priority Data

Nov. 20, 2003  (FR) ................................. 03 13612

(51) Int. Cl.
*A61K 31/381*  (2006.01)
*C07D 333/64*  (2006.01)
(52) U.S. Cl. ........................................ 514/443; 549/51
(58) Field of Classification Search .................. 549/51; 514/443

See application file for complete search history.

(56) References Cited

U.S. PATENT DOCUMENTS 5,908,859 A   6/1999  Cullinan et al.

FOREIGN PATENT DOCUMENTS

| EP | 0 897 918 A | 2/1999 |
| WO | WO 99/58519 | * 11/1999 |
| WO | WO 99/61435 A | 12/1999 |

OTHER PUBLICATIONS

Svoboda, Jiri. et al, "Application of magnesium alkoxides to syntheses of benzoheterocyclic compounds," Collection of Czechoslovak Chemical Communications (1993), vol. 58(3), pp. 592-599.*
Darias, V. et al: "Bicyclic Thiophenic Derivatives as Platelet Aggregation Inhibitors" Farmaco, Edizione Scientifica, 41(6), 478-82 Coden: FRPSAX; ISSN: 0430-0920, 1986, XP001194422.
Conde, Santiago et al.: "Analogs of Propranolol. Synthesis of 3-Alkylamino-1-(3-Benzo'b!Thienyloxy)-2-Propanols" Journal of Heterocyclic Chemistry, 17(5), 937-40 Coden: JHTCAD; ISSN: 0022-152X, 1980, XP002286806.

Witiak, Donald T. et al: "9-Chloro-2, 3-Dihydro-5H-1, 4-Dioxepino '6,5-b! Benzofuran, A Novel Antilipidemic Agent Structurally Related to Clofibrate" Journal of Medicinal Chemistry, 18(10), 992-6 CODEN: JMCMAR; ISSN: 0022-2623, 1975, XP002286807.
Connor, David T. et al: "Novel Benzothiophene-, Benzofuran-, and Naphthalenecarboxamidotetrazoles as Potential Antiallergy Agents" Journal of Medicinal Chemistry, 35(5), 958-65 CODEN: JMCMAR; ISSN: 0022-2623, 1992, XP002286756.
Tondeur, R. et al: "Benzofuran Series XXXV. Amino Derivatives of 3-Benzofuranol" Chimica Therapeutica, 3(5), 356-9 CODEN: CHTPBA; ISSN: 0009-4374, 1968, XP009033121.
Svoboda, Jiri et al.: Synthesis of '!Benzothieno'3,2-b!furan-A New Fused Benzoheterocyclic System: Collection of Czechoslovak Chemical Communications, 58(12), 2983-6 CODEN: CCCCAK; ISSN: 0010-0765, 1993, XP009033071.
Vaidya, V. P. et al: "Studies in Benzofurans: Part XIV. Synthesis of Benzofuran and Benzofuro'3,2-b!Furan Derivatives of Pharmacological Interest" Indian Journal of Chemistry, Section B: Organic Chemistry Including Medicinal Chemistry, 22b(5), 462-4 CODEN: IJSBDB; ISSN: 0376-4699, 1983, XP009033083.
Karche, Navnath P. et al: "Electronic Effects in Migratory Groups. '1,4!-Versus '1,2!-Rearrangement in Rhodium Carbenoid Generated Bicyclic Oxonium Ylides" Journal of Organic Chemistry, 66(19), 6323-6332 CODEN: Joceah; ISSN: 0022-3263, 2001, XP002286808.
Boschelli, Diane et al: "Inhibition of E-Selection-, ICAM-1-, and VCAM-1-Mediated Cell Adhesion by Benzo'b!thiophene-, Benzofuran-, Indole-, and Naphthalene-2-Carboxamides: Identification of PD 144795 as an Antiinflammatory Agent" Journal of Medicinal Chemistry, 38(22), 4597-614 CODEN: JMCMAR; ISSN: 0022-2623, 1995, XP002286757.

(Continued)

*Primary Examiner*—Kamal A. Saeed
*Assistant Examiner*—Janet L. Coppins
(74) *Attorney, Agent, or Firm*—Millen, White, Zelano & Branigan, P.C.

(57) ABSTRACT

The invention relates to compounds of the general formula (I) below:

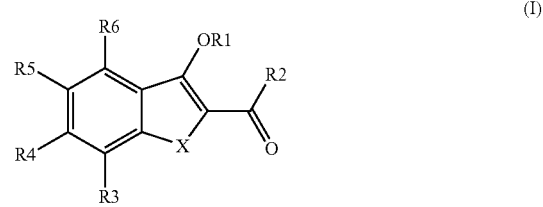

in which R1, R2, R3, R4, R5, R6 and X are as defined in claim 1.

These compounds can be used in the treatment of pathologies associated with insulin resistance syndrome.

31 Claims, No Drawings

OTHER PUBLICATIONS

Boschelli, Diane et al: "3-Alkoxybenzo'B!thiophene-2-Carboxamides as Inhibitors of Neutrophil-Endothelial Cell Adhesion" Journal of Medicinal Chemistry, 37(6), 717-18 CODEN: JMCMAR; ISSN: 0022-2623, 1994, XP002286755.

Svoboda, Jiri et al: "Application of Magnesium Alkoxides to Syntheses of Benzoheterocyclic Compounds" Collection of Czechoslovak Chemical Communications, 58(3), 592-9 CODEN: CCCCAK; ISSN: 0010-0765, 1993, XP001194423.

Norris, Robert et al: Some Studies on the Reversibility of the Association Step in SRN1 Reactions: Australian Journal of Chemistry, 38(7), 1107-16 CODEN: AJCHAS; ISSN: 0004-9425, 1985, XP009033098.

Beck James: "'1!Benzothieno'3,2-b!Furan Derivatives" Journal of Heterocyclic Chemistry, 12 (5), 1037-8 CODEN: JHTCAD; ISSN: 0022-152X, 1975, XP002286809.

* cited by examiner

ANTIDIABETIC COMPOUNDS COMPRISING BENZOFURAN AND BENZOTHIOPHENE DERIVATIVES

The present invention relates to variously substituted benzofuran and benzothiophene derivatives that are useful in the treatment of pathologies associated with insulin resistance syndrome.

The present invention relates to compounds of the general formula (I):

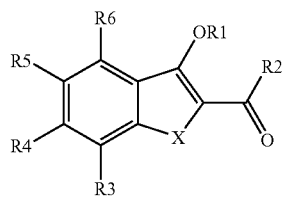

and also the stereoisomers thereof, and the racemates and pharmaceutically acceptable salts thereof, X=O or S;
R1 is chosen from:
-Alk-COOH,
-Alk-C(=O)—(O)$_m$-Ar,
-Alk-C(=O)—(O)$_m$-Het,
-Alk-C(=O)—(O)$_m$-Alk,
-Alk-C(=O)—(O)$_m$-cycloalkyl,
-Alk-C(=O)NRR',
-Alk-(O)$_m$-Ar,
-Alk-O-Alk,
-Alk-O-Alk-Ar,
-Alk-O-Het;
R2 is chosen from —OH, —OAlk, —NR7R8, —OAr, —OHet and —O-cycloalkyl;
R7 is chosen from H and -Alk;
R8 is chosen from —H;
-Alk' or -cycloalkyl,
in which Alk' or cycloalkyl is optionally substituted by one or more groups chosen from —OAlk, —CN, —OHet, —OH, —C(=O)—(O)$_m$Alk, —C(=O)—(O)$_m$Ar, —C(=O)—(O)$_m$Het, —C(=O)—(O)$_m$-cycloalkyl, —COOH and —NO$_2$;
—Ar' or Het',
in which Ar' or Het' is optionally substituted by one or more groups chosen from Hal, —OAlk, —OH, -Alk, —Ar, —OAlkAr, —OH, —CN, —OAr, —CF$_3$, -AlkAr, —COOH—NRR', -Het, —C(=O)—(O)$_m$Alk, —C(=O)—(O)$_m$Ar, —C(=O)—(O)$_m$Het, —C(=O)—(O)$_m$-cycloalkyl and NO$_2$;
or R7 and R8 form, together with the nitrogen atom to which they are attached, a nitrogenous heterocycle of 5 to 10 atoms;
R3, R4, R5 and R6, which may be identical or different, are chosen independently from H, -Hal, —OH, -Alk, —OAlk, —CN, —CF$_3$, —NRR' and —NO$_2$;
in which, in the definitions of R1-R8:
each of the Alk, which may be identical or different, is optionally and independently substituted by one or more groups chosen from -Hal, —OAlk, —Ar, —OAlkAr, —OH, —CN, —OAr, —CF$_3$, —COOH, —NRR', —C(=O)—(O)$_m$ Alk, -Het and —NO$_2$;
each of the Ar, which may be identical or different, is optionally and independently substituted by one or more groups chosen from -Hal, —OAlk, -Alk, —Ar, —OAlkAr, —OH, —CN, —OAr, —CF$_3$, -AlkAr, —COOH, —C(=O)—(O)$_m$Alk, -Alk-C(=O)—(O)$_m$Alk, —NRR', -Het, —NO$_2$, —S(O)$_n$-Ar and —S(O)$_n$Alk;
R and R' are chosen independently from H and Alk;
m=0 or 1;
n=0, 1 or 2;
with the exception of the compounds for which:
1) R1=CH$_2$-phenyl, optionally substituted by —NO$_2$ or —OMe, R2=—OMe, —OEt or —OH, R3, R6=H, R4, R5=H or —OMe, X=O or S; or
2) R1=—CH$_2$—C(=O)Me, R3, R4, R5, R6=H, X=O and R2=—OEt or X=S and R2=—OMe;
3) R1=—CH$_2$—CO$_2$Et, R2=—OEt, R3, R4, R6=H, X=O and R5=—NH$_2$ or —NO$_2$; or R1=—CH$_2$—CO$_2$Me, R3, R4, R5, R6=H, R2=—OMe and X=O or S, or R2=—OH and X=S; or
R1=—CH$_2$CO$_2$H, R3, R4, R5, R6=H, R2=OH and X=S;
4) R1=—CH$_2$-phenyl, R2=—NH$_2$, X=O, S and R5=—OMe, or X=O and R5=phenyl.

The compounds that are especially preferred are those of the general formula (I) in which:
R2=—OEt and X=S, and
R1 is chosen from:
-Alk-COOH,
-Alk-C(=O)—(O)$_m$-Ar,
-Alk-C(=O)—(O)$_m$-Het,
-Alk-C(=O)—(O)$_m$-Alk,
-Alk-C(=O)—(O)$_m$-cycloalkyl,
-Alk-C(=O)NRR',
-Alk-(O)$_m$-Ar,
-Alk-O-Alk,
-Alk-O-Alk-Ar,
-Alk-O-Het,
R3, R4, R5 and R6, which may be identical or different, are chosen independently from H, -Hal, —OH, -Alk, —OAlk, —CN, —CF$_3$, —NRR' and —NO$_2$;
in which, in the definitions of R1-R8:
each of the Alk, which may be identical or different, is optionally and independently substituted by one or more groups chosen from -Hal, —OAlk, —Ar, —OAlkAr, —OH, —CN, —OAr, —CF$_3$, —COOH, —NRR', —C(=O)—(O)$_m$Alk, -Het and —NO$_2$;
in which each of the Ar, which may be identical or different, is optionally and independently substituted by one or more groups chosen from -Hal, —OAlk, -Alk, —Ar, —OAlkAr, —OH, —CN, —OAr, —CF$_3$, -AlkAr, —COOH, —C(=O)—(O)$_m$Alk, -Alk-C(=O)—(O)$_m$Alk, —NRR', -Het, —NO$_2$, —S(O)$_n$-Ar and —S(O)$_n$Alk;
R and R' are chosen independently from H and Alk;
m=0 or 1;
n=0, 1 or 2.

According to another subject, the preferred compounds of the general formula (I) are also those in which
X=O or S;
R1 is chosen from:
-Alk-COOH,
-Alk-C(=O)—(O)$_m$-Ar,
-Alk-C(=O)—(O)$_m$-Het,
-Alk-C(=O)—(O)$_m$-Alk,
-Alk-C(=O)—(O)$_m$-cycloalkyl,
-Alk-C(=O)NRR',
-Alk-(O)$_m$-Ar,
-Alk-O-Alk,
-Alk-O-Alk-Ar,
-Alk-O-Het;
R2=—NR7R8 in which R7 is chosen from H and -Alk;
R8 is chosen from
-Alk' and -cycloalkyl,
in which Alk' or cycloalkyl is optionally substituted by one or more groups chosen from —OAlk, —CN, —OHet, —OH, —C(=O)—(O)$_m$Alk, —C(=O)—(O)$_m$Ar, —C(=O)—(O)$_m$Het, —C(=O)—(O)$_m$-cycloalkyl, —COOH and —NO$_2$;
—Ar' or Het';
in which Ar' or Het' is optionally substituted by one or more groups chosen from Hal, —OAlk, —OH, -Alk, —Ar, —OAlkAr, —OH, —CN, —OAr, —CF$_3$, -AlkAr, —COOH—NRR', -Het, —C(=O)—(O)$_m$Alk, —C(=O)—(O)$_m$Ar, —C(=O)—(O)$_m$Het, —C(=O)—(O)$_m$-cycloalkyl and NO$_2$;

R3, R4, R5 and R6, which may be identical or different, are chosen independently from H, -Hal, —OH, -Alk, —OAlk, —CN, —CF$_3$, —NRR' and —NO$_2$;
in which each of the Alk, which may be identical or different, is optionally and independently substituted by one or more groups chosen from -Hal, —OAlk, —Ar, —OAlkAr, —OH, —CN, —OAr, —CF$_3$, —COOH, —NRR', —C(=O)—(O)$_m$Alk, -Het and —NO$_2$;
in which each of the Ar, which may be identical or different, is optionally and independently substituted by one or more groups chosen from -Hal, —OAlk, -Alk, —Ar, —OAlkAr, —OH, —CN, —OAr, —CF$_3$, -AlkAr, —COOH, —C(=O)—(O)$_m$Alk, -Alk-C(=O)—(O)$_m$Alk, —NRR', -Het, —NO$_2$, —S(O)$_n$-Ar and -S(O)$_n$Alk;
R and R' are chosen independently from H and Alk;
m=0 or 1;
n=0, 1 or 2;
X=O or S;
R1 is chosen from:
-Alk-COOH,
-Alk-C(=O)—(O)$_m$-Ar,
-Alk-C(=O)—(O)$_m$-Het,
-Alk-C(=O)—(O)$_m$-Alk,
-Alk-C(=O)—(O)$_m$-cycloalkyl,
-Alk-C(=O)NRR',
-Alk-(O)$_m$-Ar,
-Alk-O-Alk,
-Alk-O-Alk-Ar,
-Alk-O-Het.
For any one of the definitions given above,
Preferably, R3, R4, R5, R6=H.
Preferably, X=S.
Preferably, R2=—OAlk.
Preferably, m=0;
Preferably R2=—NR7R8
in which
R7=H or Alk and
R8=-Alk' optionally substituted by —C(=O)—OAlk,
-Het', —Ar' optionally substituted by -Hal, —C(=O)OAlk or -Alk-C(=O)OAlk.
Preferably, R1=—CH$_2$—COOH, —CH$_2$—C(=O)—(O)$_m$-Ar, —CH$_2$—C(=O)—(O)$_m$Het, —CH$_2$—C(=O)—(O)$_m$-Alk, —CH$_2$—C(=O)NRR', —CH$_2$—(O)$_m$-Ar, —CH$_2$—O-Alk, —CH$_2$—O-Alk-Ar or —CH$_2$—O-Het,
in which
Ar, preferably phenyl, is optionally substituted by one or more groups chosen from Hal, —OAlk, —Ar, -Alk, —O-Alk-Ar, —C(=O)—(O)$_m$-Alk, -Alk-C(=O)—(O)$_m$Alk, —S(O)$_n$-Ar, —S(O)$_n$-Alk, —O—CF$_3$, —CN and —OH,
in which m=0 or 1, and n=2.
Even more preferably, R1=—CH$_2$—C(=O)—Ar, —CH$_2$—C(=O)-Alk or —(CH$_2$)$_m$-(O)$_m$-Ar, in which Ar, preferably phenyl, is optionally substituted by one or more groups chosen from Hal, —OAlk, —Ar, -Alk, —O-Alk-Ar, —C(=O)—(O)$_m$-Alk, -Alk-C(=O)—(O)$_m$Alk, —S(O)$_n$-Ar, —S(O)$_n$-Alk, —O—CF$_3$, —CN and —OH,
in which m=0 or 1, m'=1 or 2, n=2.
Preferably m'=2 if m=1.
Advantageously, R1=—CH$_2$—C(=O) Alk, in which preferably, Alk=—CMe$_3$;
Advantageously, R1=—CH$_2$—C(=O)-phenyl or —CH$_2$-phenyl, in which phenyl is optionally substituted by one or more groups chosen from -Hal, —OAlk and —CN.

The compounds of the formula (i) may be chosen especially from:
ethyl 3-[2-(4-chlorophenyl)-2-oxoethoxy]benzo[b]thiophene-2-carboxylate;
ethyl 3-(2-oxo-2-phenylethoxy)benzo[b]thiophene-2-carboxylate;
ethyl 3-[2-(2-methoxyphenyl)-2-oxoethoxy]benzo[b]thiophene-2-carboxylate;
ethyl 3-(2-biphenyl-4-yl-2-oxoethoxy)benzo[b]thiophene-2-carboxylate;
ethyl 3-(2-oxo-2-p-tolylethoxy)benzo[b]thiophene-2-carboxylate;
ethyl 3-(2-adamantan-1-yl-2-oxoethoxy)benzo[b]thiophene-2-carboxylate;
ethyl 3-[2-(4-fluorophenyl)-2-oxoethoxy]benzo[b]thiophene-2-carboxylate;
ethyl 3-[2-(3-methoxyphenyl)-2-oxoethoxy]benzo[b]thiophene-2-carboxylate;
ethyl 3-[2-(4-benzyloxyphenyl)-2-oxoethoxy]benzo[b]thiophene-2-carboxylate;
ethyl 3-(1-methyl-2-oxo-2-phenylethoxy)benzo[b]thiophene-2-carboxylate;
ethyl 3-[2-(2,4-dimethoxyphenyl)-2-oxoethoxy]benzo[b]thiophene-2-carboxylate;
ethyl 3-(3,3-dimethyl-2-oxobutoxy)benzo[b]thiophene-2-carboxylate;
ethyl 3-(2-naphthalen-2-yl-2-oxoethoxy)benzo[b]thiophene-2-carboxylate;
3-[2-(2,3-dichloro-4-methoxyphenyl)-2-oxoethoxy]benzo[b]thiophene-2-carboxylate;
ethyl 3-[2-(2-benzyloxy-5-fluorophenyl)-2-oxoethoxy]benzo[b]thiophene-2-carboxylate;
ethyl 3-hydroxybenzo[b]thiophene-2-carboxylate;
ethyl 3-[2-(4-fluorophenoxy)ethoxy]benzo[b]thiophene-2-carboxylate;
ethyl 3-phenethyloxybenzo[b]thiophene-2-carboxylate;
ethyl 3-(2-phenoxyethoxy)benzo[b]thiophene-2-carboxylate;
ethyl 3-[2-(4-cyanophenoxy)ethoxy]benzo[b]thiophene-2-carboxylate;
ethyl 3-{2-[4-(2-methoxycarbonylethyl)phenoxy]ethoxy}benzo[b]thiophene-2-carboxylate;
ethyl 3-[2-(naphthalen-1-yloxy)ethoxy]benzo[b]thiophene-2-carboxylate;
ethyl 3-[2-(2-methoxyphenoxy)ethoxy]benzo[b]thiophene-2-carboxylate;
ethyl 3-[2-(2,3-dimethylphenoxy)ethoxy]benzo[b]thiophene-2-carboxylate;
ethyl 3-(2'-cyanobiphenyl-4-ylmethoxy)benzo[b]thiophene-2-carboxylate;
ethyl 3-(2-hydroxy-3-phenoxypropoxy)benzo[b]thiophene-2-carboxylate;
ethyl 3-(3-phenoxypropoxy)benzo[b]thiophene-2-carboxylate;
ethyl 3-(2-cyanobenzyloxy)benzo[b]thiophene-2-carboxylate;

ethyl 3-(3-cyanobenzyloxy)benzo[b]thiophene-2-carboxylate;
ethyl 3-(4-cyanobenzyloxy)benzo[b]thiophene-2-carboxylate;
ethyl 3-(2-benzenesulfonylmethylbenzyloxy)benzo[b]thiophene-2-carboxylate;
ethyl 3-(4-methoxycarbonylbenzyloxy)benzo[b]thiophene-2-carboxylate;
ethyl 3-(4-trifluoromethoxybenzyloxy)benzo[b]thiophene-2-carboxylate;
ethyl 3-pentafluorophenylmethoxybenzo[b]thiophene-2-carboxylate;
ethyl 3-(4-trifluoromethylbenzyloxy)benzo[b]thiophene-2-carboxylate;
ethyl 3-(naphthalen-2-ylmethoxy)benzo[b]thiophene-2-carboxylate;
ethyl 3-(biphenyl-2-ylmethoxy)benzo[b]thiophene-2-carboxylate;
ethyl 3-(3-methoxybenzyloxy)benzo[b]thiophene-2-carboxylate;
ethyl 3-(4-fluorobenzyloxy)benzo[b]thiophene-2-carboxylate;
ethyl 3-(4-bromobenzyloxy)benzo[b]thiophene-2-carboxylate;
ethyl 3-(4-methylbenzyloxy)benzo[b]thiophene-2-carboxylate;
ethyl 3-benzyloxybenzo[b]thiophene-2-carboxylate;
ethyl 3-(2,3-difluorobenzyloxy)benzo[b]thiophene-2-carboxylate;

and also the stereoisomeric forms, and the racemates and pharmaceutically acceptable salts thereof.

Preferably, the compounds of the formula (i) are chosen from:
ethyl 3-[2-(2-methoxyphenyl)-2-oxoethoxy]benzo[b]thiophene-2-carboxylate;
ethyl 3-[2-(4-fluorophenyl)-2-oxoethoxy]benzo[b]thiophene-2-carboxylate;
ethyl 3-[2-(3-methoxyphenyl)-2-oxoethoxy]benzo[b]thiophene-2-carboxylate;
ethyl 3-(1-methyl-2-oxo-2-phenylethoxy)benzo[b]thiophene-2-carboxylate;
ethyl 3-[2-(2,4-dimethoxyphenyl)-2-oxoethoxy]benzo[b]thiophene-2-carboxylate;
ethyl 3-(3,3-dimethyl-2-oxobutoxy)benzo[b]thiophene-2-carboxylate;
ethyl 3-(2-naphthalen-2-yl-2-oxoethoxy)benzo[b]thiophene-2-carboxylate;
ethyl 3-(3-cyanobenzyloxy)benzo[b]thiophene-2-carboxylate;

and also the stereoisomeric forms, and the racemates and pharmaceutically acceptable salts thereof.

According to the present invention, the radical -Alk or -Alk' represents an alkyl radical, i.e. a saturated hydrocarbon-based radical in a straight or branched chain of 1 to 20 carbon atoms and preferably of 1 to 5 carbon atoms.

If they are linear, mention may be made especially of methyl, ethyl, propyl, butyl, pentyl, hexyl, octyl, nonyl, decyl, dodecyl, hexadecyl and octadecyl radicals.

If they are branched or substituted by one or more alkyl radicals, mention may be made especially of isopropyl, tert-butyl, 2-ethylhexyl, 2-methylbutyl, 2-methylpentyl, 1-methylpentyl and 3-methylheptyl radicals.

Among the halogen atoms, mention is made more particularly of fluorine, chlorine, bromine and iodine atoms, preferably fluorine.

The cycloalkyl or cycloalkyl' radical is a mono-, bi- or tricyclic, saturated or partially unsaturated, non-aromatic hydrocarbon-based radical of 3 to 10 carbon atoms, such as, especially, cyclopropyl, cyclopentyl, cyclohexyl or adamantyl, and also the corresponding rings containing one or more unsaturations.

Ar or Ar' represents an aryl radical, i.e. a mono- or bicyclic hydrocarbon-based aromatic system of 6 to 10 carbon atoms.

Among the aryl radicals that may especially be mentioned are the phenyl or naphthyl radical, more particularly substituted by at least one halogen atom.

Among the radicals -AlkAr(-alkylaryl), mention may be made especially of the benzyl or phenethyl radical.

Het or Het' represents a heteroaryl radical, i.e. a mono- or bicyclic aromatic system of 5 to 10 carbon atoms, comprising one or more hetero atoms chosen from nitrogen, oxygen and sulfur. Among the heteroaryl radicals that may be mentioned are pyrazinyl, thienyl, oxazolyl, furazanyl, pyrrolyl, 1,2,4-thiadiazolyl, naphthyridinyl, pyridazinyl, quinoxalinyl, phthalazinyl, imidazo[1,2-a]pyridinyl, imidazo[2,1-b]thiazolyl, cinnolinyl, triazinyl, benzofurazanyl, azaindolyl, benzimidazolyl, benzothienyl, thienopyridyl, thienopyrimidinyl, pyrrolopyridyl, imidazopyridyl, benzazaindolyl, 1,2,4-triazinyl, benzothiazolyl, furanyl, imidazolyl, indolyl, triazolyl, tetrazolyl, indolizinyl, isoxazolyl, isoquinolyl, isothiazolyl, oxadiazolyl, pyrazinyl, pyridazinyl, pyrazolyl, pyridyl, pyrimidinyl, purinyl, quinazolinyl, quinolyl, isoquinolyl, 1,3,4-thiadiazolyl, thiazolyl, triazinyl, isothiazolyl and carbazolyl, and also the corresponding groups derived from their fusion or from fusion with the phenyl nucleus. The preferred heteroaryl groups include thienyl, pyrrolyl, quinoxalinyl, furanyl, imidazolyl, indolyl, isoxazolyl, isothiazolyl, pyrazinyl, pyridazinyl, pyrazolyl, pyridyl, pyrimidinyl, quinazolinyl, quinolinyl, thiazolyl, carbazolyl and thiadiazolyl, and groups derived from fusion with a phenyl nucleus, and more particularly quinolyl, carbazolyl and thiadiazolyl.

Hal denotes a halogen atom, chosen from chlorine, fluorine, iodine and bromine.

The expression "pharmaceutically acceptable salts" refers to the relatively non-toxic mineral and organic acid-addition salts, and the base-addition salts, of the compounds of the present invention. These salts can be prepared in situ during the final isolation and purification of the compounds. In particular, the acid-addition salts can be prepared by separately reacting the purified compound in its purified form with an organic or mineral acid and isolating the salt thus formed. Among the examples of acid-addition salts are the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactobionate, sulfamates, malonates, salicylates, propionates, methylenebis-b-hydroxynaphthoates, gentisic acid, isethionates, di-p-toluoyltartrates, methanesulfonates, ethanesulfonates, benzenesulfonates, p-toluenesulfonates, cyclohexyl sulfamates and quinates-laurylsulfonate, and analogues. (See for example S. M. Berge et al. "Pharmaceutical Salts" *J. Pharm. Sci*, 66: pp. 1-19 (1977) which is incorporated herein by reference). The acid-addition salts can also be prepared by separately reacting the purified compound in its acid form with an organic or mineral base and isolating the salt thus formed. The acid-addition salts include amine salts and metal salts. The suitable metal salts include the sodium, potassium, calcium, barium, zinc, magnesium and aluminium salts. The sodium and potassium salts are preferred. The suitable mineral base-addition salts are prepared from metallic bases including sodium hydride, sodium hydroxide, potassium hydroxide, calcium hydroxide, aluminium hydroxide, lithium hydroxide, magnesium hydroxide and zinc hydroxide. The suitable amine base-addition salts are prepared from amines whose basicity is sufficient to form a stable salt, and preferably include amines that are often used in medicinal chemistry on account of their low toxicity and their acceptability for medical use: ammonia, ethylenediamine, N-methylglucamine, lysine, arginine, ornithine, choline, N,N'-dibenzylethylenediamine, chloroprocaine, diethanolamine, procaine, N-benzyl-phenethylamine, diethylamine, piperazine, tris(hydroxymethyl)aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, for example lysine and arginine, and dicyclohexylamine, and analogues.

The compounds of the invention of the formula (I) as defined above containing a sufficiently acidic function or a sufficiently basic function, or both, can include the corresponding pharmaceutically acceptable salts of an organic or mineral acid or of an organic or mineral base.

The compounds of the general formula (I) can be prepared by application or adaptation of any method known per se and/or within the capacity of a person skilled in the art, especially those described by Larock in *Comprehensive Organic Transformations*, VCH Pub., 1989, or by application or adaptation of the processes described in the examples that follow.

According to another subject, the invention also relates to the preparation of the compounds of the formula (I) described hereinabove, according to the methodology described hereinbelow.

The compounds of the general formula (I) can especially be prepared according to the synthetic route:

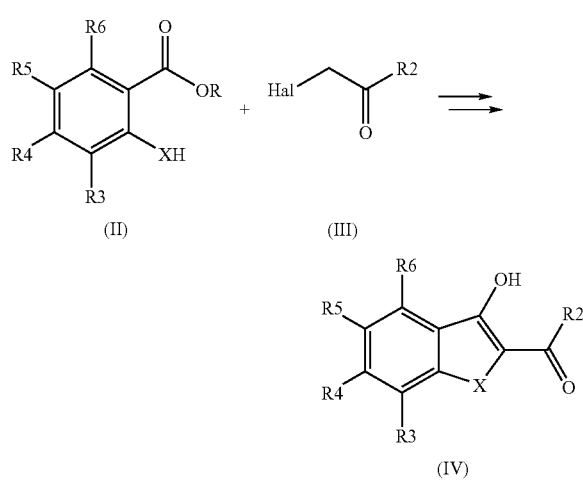

1—Addition of a (thio)salicylic acid derivative of the formula (II)

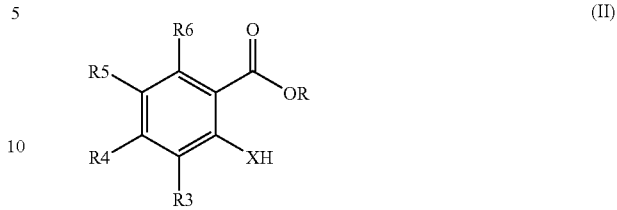

in which R3-R6 and X are as defined above, and R represents a hydrogen atom or an alkyl radical, to a 2-haloethanone derivative of the formula (III):

in which Hal represents a halogen atom and R2 is as defined above, in a polar solvent, such as ethanol, at a temperature of from −20 to 200° C., more particularly 0-20° C., followed by cyclization in a polar solvent, such as methanol, water, DMF, NMP, DMSO or iPrOH, preferably DMF at a temperature of from −20 to 200° C., more particularly 0-200° C., preferably in the presence of sodium acetate, 2—Coupling of the resultant derivative (IV)

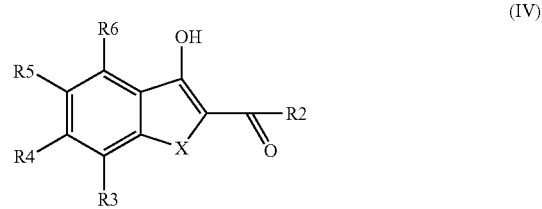

with a halo derivative of the formula (V):

on an equimolar basis, in a polar solvent, such as ethanol, methanol, water, DMF, NMP, DMSO or iPrOH, preferably DMF, at a temperature of from −20 to 200° C., more particularly 0-200° C.

The mode of addition of a salicylic acid to a 2-bromoacetophenone derivative is described especially by Gayral, Buisson et al. in Eur. J. Med. Chem. Chim. Ther.; FR; 20; 2; 1985; 187-189. The coupling step has been described especially by Blicke in J. Am. Chem. Soc.; EN; 71; 1949; 2856-2858.

The said process may optionally also include the step consisting in isolating the product obtained.

In the reactions described hereinbelow, it may be necessary to protect reactive functional groups, for example hydroxyl, amino, imino, thio or carboxyl groups, if they are desired in the final product, to avoid their unwanted participation in the reactions. The conventional protecting groups can be used in accordance with the standard practice; for examples, see T. W. Green and P. G. M. Wuts in *Protective*

*Groups in Organic Chemistry*, John Wiley and Sons, 1991; J. F. W. McOmie in *Protective Groups in Organic Chemistry*, Plenum Press, 1973.

The compound thus prepared can be recovered from the reaction mixture via the conventional means. For example, the compounds can be recovered by distilling the solvent from the reaction mixture or, if necessary, after distilling off the solvent from the mixture of the solution, pouring the remainder into water, followed by extraction with a water-immiscible organic solvent, and distilling the solvent from the extract. In addition, the product can also be purified, if so desired, by various techniques, such as recrystallization, reprecipitation or various chromatographic techniques, especially column chromatography or preparative thin-layer chromatography.

It will be appreciated that the compounds that are useful according to the present invention may contain asymmetric centres. These asymmetric centres may be, independently, of R or S configuration. It will be apparent to a person skilled in the art that certain compounds that are useful according to the invention may also exhibit geometrical isomerism. It should be understood that the present invention includes individual geometrical isomers and stereoisomers, and mixtures thereof, including racemic mixtures, of compounds of the formula (I) above. These isomers can be separated from their mixtures by application or adaptation of known processes, for example chromatography techniques or recrystallization techniques, or they are prepared separately from suitable isomers of their intermediates.

For the purposes of the present text, it is understood that the tautomeric forms are included in the citation of a given group, for example thio/mercapto or oxo/hydroxyl.

The acid-addition salts are formed with the compounds that are useful according to the invention in which a basic function, such as an amino, alkylamino or dialkylamino group, is present. The pharmaceutically acceptable, i.e. non-toxic, acid-addition salts are preferred. The selected salts are optimally chosen so as to be compatible with the usual pharmaceutical vehicles and suitable for oral or parenteral administration. The acid-addition salts of the compounds that are useful according to the present invention can be prepared by reacting the free base with the appropriate acid, by application or adaptation of known processes. For example, the acid-addition salts of the compounds that are useful according to the present invention can be prepared either by dissolving the free base in water or in a basified aqueous solution or suitable solvents containing the appropriate acid, and isolating the solvent by evaporating the solution, or by reacting the free base and the acid in an organic solvent, in which case the salt separates out directly or can be obtained by concentrating the solution. Among the acids that are suitable for use in the preparation of these salts are hydrochloric acid, hydrobromic acid, phosphoric acid, sulfuric acid, various organic carboxylic and sulfonic acids, such as acetic acid, citric acid, propionic acid, succinic acid, benzoic acid, tartaric acid, fumaric acid, mandelic acid, ascorbic acid, malic acid, methanesulfonic acid, toluenesulfonic acid, fatty acids, adipate, alginate, ascorbate, aspartate, benzenesulfonate, benzoate, cyclopentanepropionate, digluconate, dodecyl sulfate, bisulfate, butyrate, lactate, laurate, lauryl sulfate, malate, hydriodide, 2-hydroxyethanesulfonate, glycerophosphate, picrate, pivalate, pamoate, pectinate, persulfate, 3-phenylpropionate, thiocyanate, 2-naphthalenesulfonate, undecanoate, nicotinate, hemisulfate, heptonate, hexanoate, camphorate, camphorsulfonate and the like.

The acid-addition salts of the compounds that are useful according to the present invention can be regenerated from the salts by application or adaptation of known processes. For example, the parent compounds that are useful according to the invention can be regenerated from their acid-addition salts by treatment with an alkali, for example aqueous sodium bicarbonate solution or aqueous ammonia solution.

The compounds that are useful according to the present invention can be regenerated from their base-addition salts by application or adaptation of known processes. For example, the parent compounds that are useful according to the invention can be regenerated from their base-addition salts by treatment with an acid, for example hydrochloric acid.

The base-addition salts may be formed if the compound that is useful according to the invention contains a carboxyl group, or a sufficiently acidic bioisostere. The bases that can be used to prepare the base-addition salts preferably include those that produce, if they are combined with a free acid, pharmaceutically acceptable salts, i.e. salts whose cations are not toxic to the patient in the pharmaceutical doses of the salts, such that the beneficial inhibitory effects intrinsic to the free base are not negated by the side effects attributable to the cations. The pharmaceutically acceptable salts, including those derived from alkaline-earth metal salts, within the scope of the present invention include those derived from the following bases: sodium hydride, sodium hydroxide, potassium hydroxide, calcium hydroxide, aluminium hydroxide, lithium hydroxide, magnesium hydroxide, zinc hydroxide, ammonia, ethylenediamine, N-methylglucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, tetramethylammonium hydroxide and the like.

The compounds that are useful according to the present invention can be readily prepared, or formed during the process of the invention, in the form of solvates (for example hydrates). The hydrates of the compounds that are useful according to the present invention can be readily prepared by recrystallization of an aqueous/organic solvent mixture, using organic solvents, such as dioxane, tetrahydrofuran or methanol.

The basic products or the intermediates can be prepared by application or adaptation of known processes, for example processes as described in the Reference Examples or obvious chemical equivalents thereof.

According to the present invention, the compounds of the formula (I) have hypoglycaemiant activity. They can reduce hyperglycaemia, more particularly the hyperglycaemia of non-insulin-dependent diabetes.

Insulin resistance is characterized by a reduction in the action of insulin (cf. Presse Médicale, 1997, 26 (No 14), 671-677) and is involved in a large number of pathological conditions, such as diabetes and more particularly noninsulin-dependent diabetes (type II diabetes or NIDDM), dyslipidaemia, obesity and certain microvascular and macrovascular complications, for instance atherosclerosis, arterial hypertension, inflammatory processes, macroangiopathy, microangiopathy, retinopathy and neuropathy.

In this respect, reference will be made, for example, to Diabetes, vol. 37, 1988, 1595-1607; *Journal of Diabetes and Its Complications,* 1998, 12, 110-119 or Horm. Res., 1992, 38, 28-32.

In particular, the compounds of the invention show strong hypoglycaemiant activity.

The compounds of the formula (I) are thus useful in the treatment of hyperglycaemia-related pathologies.

The present invention thus also relates to pharmaceutical compositions comprising, as active principle, a compound according to the invention.

The pharmaceutical compositions according to the invention can be presented in forms intended for parenteral, oral, rectal, permucous or percutaneous administration.

They will thus be presented in the form of injectable solutions or suspensions or multi-dose bottles, in the form of plain or coated tablets, sugar-coated tablets, wafer capsules, gel capsules, pills, cachets, powders, suppositories or rectal capsules, solutions or suspensions, for percutaneous use in a polar solvent, or for permucous use.

The excipients that are suitable for such administrations are cellulose or microcrystalline cellulose derivatives, alkaline-earth metal carbonates, magnesium phosphate, starches, modified starches and lactose for solid forms.

For rectal use, cocoa butter or polyethylene glycol stearates are the preferred excipients.

For parenteral use, water, aqueous solutions, physiological saline and isotonic solutions are the vehicles most appropriately used.

The dosage may vary within wide ranges (0.5 mg to 1000 mg) according to the therapeutic indication and the route of administration, and also to the age and weight of the patient.

In the case of non-insulin-dependent diabetes, in man, hyperglycaemia is the results of two major defects: an impairment in insulin secretion and a reduction in the efficacy of insulin at three sites (liver, muscles and adipose issue).

By increasing insulin secretion by the pancreatic beta cells, the compounds of the present invention are thus capable of improving the glycaemia of non-insulin-dependent diabetic patients.

The examples that follow illustrate the invention without, however, limiting it.

I. Preparation of the Compounds of the Formula (I)

The starting materials used are known products or are prepared according to known processes.

EXAMPLE OF THE PREPARATION OF A COMPOUND OF THE FORMULA (I)

Preparation of sodium 2-ethoxycarbonylmethylsulfanylbenzoate 21.580 ml (0.191 mol) of ethyl bromoacetate and 15.960 g (0.195 mol) of sodium acetate are added to 30 g (0.189 mol) of thiosalicylic acid $C_7H_6O_2S$ in 180 ml of ethanol. The reaction is stirred for 1 hour at room temperature. The mixture is diluted with water and the compound is filtered off, washed with water and dried to give 44.61 g (0.186 mol, 98.2%) of a white solid (used without further purification for the following step).

25.590 g (0.312 mol) of sodium acetate are added to 37.4 g (0.156 mol) of the crude product in 200 ml of DMF. The reaction is refluxed for 1 hour. The mixture is diluted with water and the precipitate formed is washed with water, dried under vacuum and then dissolved in 200 ml of butanol. 46.3 ml (0.156 mol) of sodium ethoxide are added. The reaction is stirred for 1 hour at room temperature, and the product is filtered off, washed with butanol and then dried to give 25.5 g (0.103 mol, 66.1%) of $C_{11}H_9NaO_3S$.

Preparation of ethyl 3-(3,3-dimethyl-2-oxobutoxy) benzo[b]thiophene-2-carboxylate A pinch of NaI crystals is added to 22.22 g (90.972 mmol) of $C_{11}H_9NaO_3S$ in 250 ml of DMF, followed by addition of 15.610 ml (113.715 mmol) of 1-bromopinacolone. The mixture is stirred at room temperature for 5 hours. The product is extracted with ethyl acetate. The organic phases are washed with water, with saturated NaCl solution and dried over $Na_2SO_4$, and then concentrated to give 27 g (0.084 mol, 84%) of a white powder.

By way of example, the compounds listed in Table A were prepared according to the procedures described above.

The formulae and characteristics of the compounds of the formula (I) are collated in Table A.

TABLE A

Hewlett Packard LC/MSD (Simple Quad)- Orthogonal Spray - Source APCL, HP Series 1100 line with diode array.

| Products | Structure | Formula | Molecular weight (g.mol$^{-1}$) | MS | Purity (%) | Tr (Min) | 1H NMR 200 MHz DMSOd6 (δ ppm) |
|---|---|---|---|---|---|---|---|
| 1 | 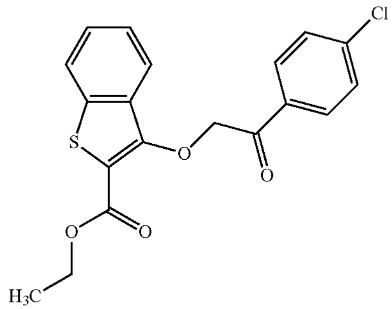 | C$_{19}$H$_{15}$ClO$_4$S | 374.85 | M + 1 = 375 | 85.6 | 4.94 | |
| 2 | 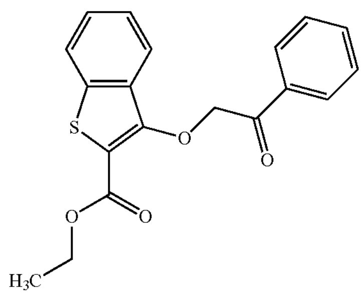 | C$_{19}$H$_{16}$O$_4$S | 340.40 | M + 1 = 341 | 86 | 3.22 | |
| 3 | 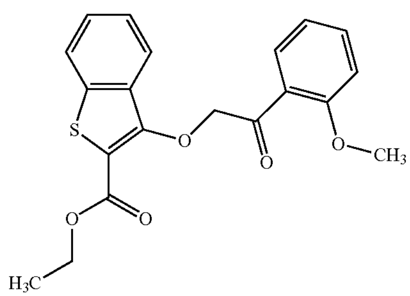 | C$_{20}$H$_{18}$O$_5$S | 370.43 | M + 1 = 371 | 94 | 3.38 | |

TABLE A-continued
Hewlett Packard LC/MSD (Simple Quad)- Orthogonal Spray - Source APCI, HP Series 1100 line with diode array.
| Products | Structure | Formula | Molecular weight (g.mol$^{-1}$) | MS | Purity (%) | Tr (Min) | 1H NMR 200 MHz DMSOd6 (δ ppm) |
|---|---|---|---|---|---|---|---|
| 4 | 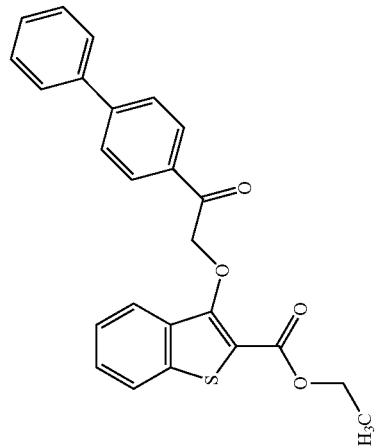 | $C_{25}H_{20}O_4S$ | 416.50 | M + 1 = 417 | 83 | 8.27 | |
| 5 | 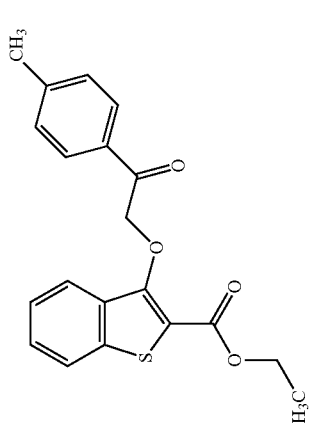 | $C_{20}H_{18}O_4S$ | 354.43 | M + 1 = 355 | 89.1 | 4.06 | |

TABLE A-continued

Hewlett Packard LC/MSD (Simple Quad)- Orthogonal Spray - Source APCL, HP Series 1100 line with diode array.

| Products | Structure | Formula | Molecular weight (g.mol$^{-1}$) | MS | Purity (%) | Tr (Min) | 1H NMR 200 MHz DMSOd6 (δ ppm) |
|---|---|---|---|---|---|---|---|
| 6 | 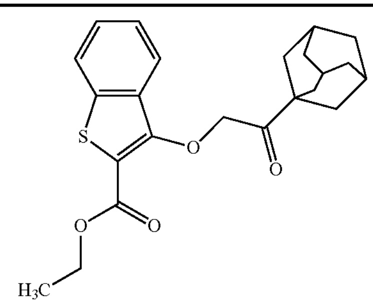 | $C_{23}H_{26}O_4S$ | 398.53 | M + 1 = 399 | 92.2 | 1.27 | |
| 7 | 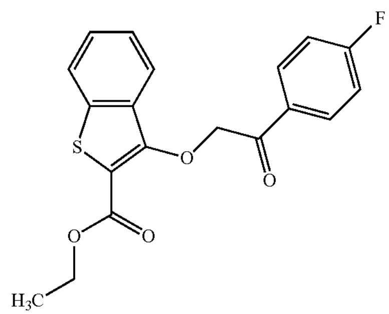 | $C_{19}H_{15}FO_4S$ | 358.39 | M + 1 = 359 | 94.2 | 3.33 | |
| 8 | 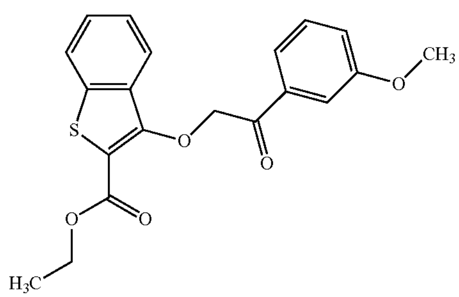 | $C_{20}H_{18}O_5S$ | 370.43 | M + 1 = 371 | 94.6 | 3.62 | |

TABLE A-continued

Hewlett Packard LC/MSD (Simple Quad)- Orthogonal Spray - Source APCI, HP Series 1100 line with diode array.

| Products | Structure | Formula | Molecular weight (g.mol$^{-1}$) | MS | Purity (%) | Tr (Min) | 1H NMR 200 MHz DMSOd6 (δ ppm) |
|---|---|---|---|---|---|---|---|
| 9 | 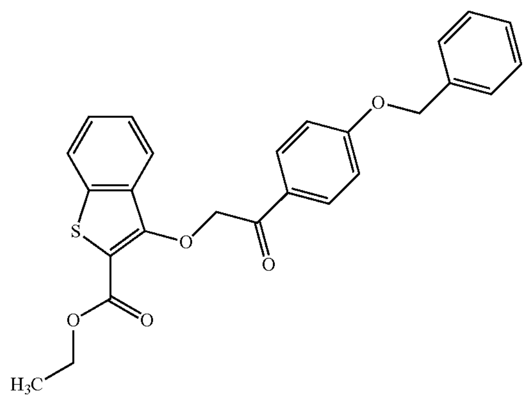 | C$_{26}$H$_{22}$O$_5$S | 446.53 | M + 1 = 447 | 94 | 7.25 | |
| 10 | 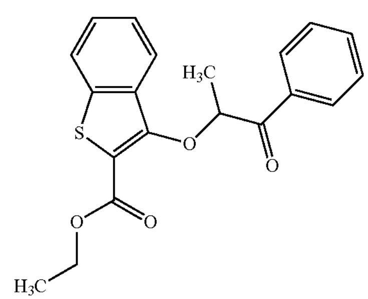 | C$_{20}$H$_{18}$O$_4$S | 354.43 | M + 1 = 355 | 89 | 3.82 | |

TABLE A-continued

Hewlett Packard LC/MSD (Simple Quad)- Orthogonal Spray - Source APCI, HP Series 1100 line with diode array.

| Products | Structure | Formula | Molecular weight (g.mol$^{-1}$) | MS | Purity (%) | Tr (Min) | 1H NMR 200 MHz DMSOd6 (δ ppm) |
|---|---|---|---|---|---|---|---|
| 11 | 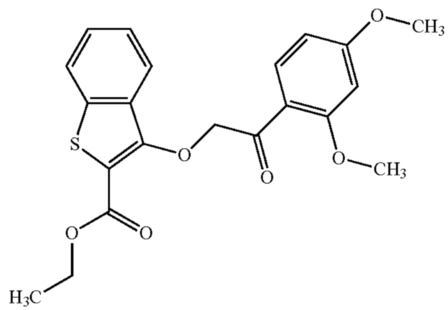 | C$_{21}$H$_{20}$O$_6$S | 400.45 | M + 1 = 401 | 95.6 | 3.44 | |
| 12 | 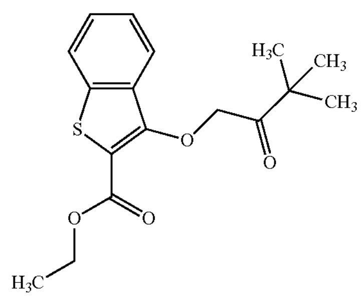 | C$_{17}$H$_{20}$O$_4$S | 320.41 | | | | |
| 13 | 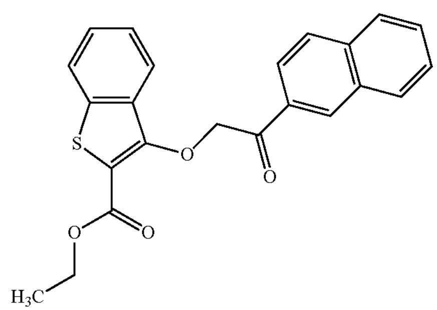 | C$_{23}$H$_{18}$O$_4$S | 390.46 | M + 1 = 391 | 88.4 | 6.02 | |

TABLE A-continued
Hewlett Packard LC/MSD (Simple Quad)- Orthogonal Spray - Source APCI, HP Series 1100 line with diode array.
| Products | Structure | Formula | Molecular weight (g.mol$^{-1}$) | MS | Purity (%) | Tr (Min) | 1H NMR 200 MHz DMSOd6 (δ ppm) |
|---|---|---|---|---|---|---|---|
| 14 | 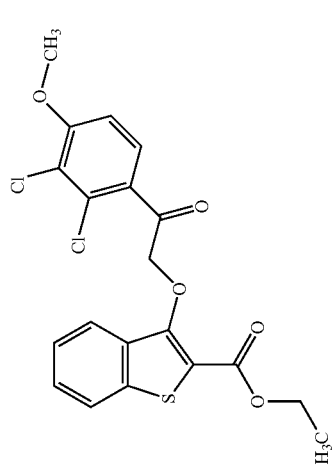 | C$_{20}$H$_{16}$Cl$_2$O$_5$S | 439.32 | M + 1 = 439 | 89.8 | 5.95 | |
| 15 | 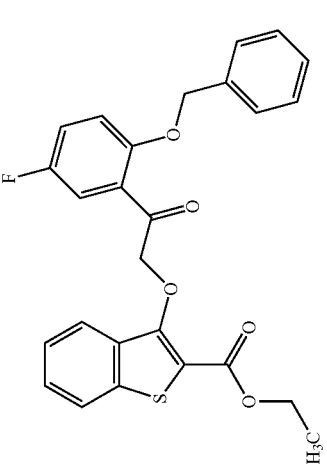 | C$_{26}$H$_{21}$FO$_5$S | 464.52 | M + 1 = 465 | 84.7 | 6.37 | |

TABLE A-continued
Hewlett Packard LC/MSD (Simple Quad)- Orthogonal Spray - Source APCI, HP Series 1100 line with diode array.
| Products | Structure | Formula | Molecular weight (g.mol$^{-1}$) | MS | Purity (%) | Tr (Min) | 1H NMR 200 MHz DMSOd6 (δ ppm) |
|---|---|---|---|---|---|---|---|
| 16 | 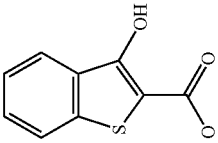 | $C_{11}H_{10}O_3S$ | 222.26 | | | | 1.31 (t, 3H) 4.34 (q, 2H) 7.44 (m, 2H) 7.91 (m, 2H) 10.58 (s, 1H) |
| 17 | 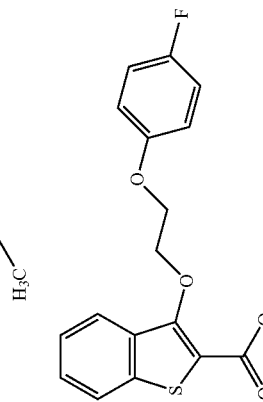 | $C_{19}H_{17}FO_4S$ | 360.41 | M + 1 = 361 | 98.8 | 4.46 | 1.34 (t, 3H) 4.35 (m, 4H) 4.66 (t, 2H) 6.88 (m, 2H) 7.14 (m, 2H) 7.55 (m, 2H) 7.99 (m, 2H) |
| 18 | 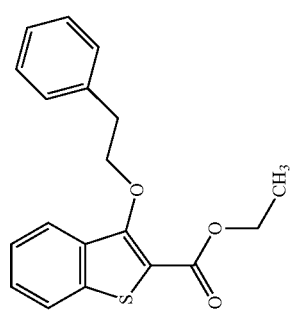 | $C_{19}H_{18}O_3S$ | 326.42 | M + 1 = 327 | 86 | 5.96 | 1.35 (t, 3H) 3.16 (t, 2H) 4.37 (q, 2H) 4.55 (t, 2H) 7.39 (m, 8H) 8.01 (m, 1H) |

TABLE A-continued

Hewlett Packard LC/MSD (Simple Quad)- Orthogonal Spray - Source APCI, HP Series 1100 line with diode array.

| Products | Structure | Formula | Molecular weight (g.mol$^{-1}$) | MS | Purity (%) | Tr (Min) | 1H NMR 200 MHz DMSOd6 (δ ppm) |
|---|---|---|---|---|---|---|---|
| 19 | 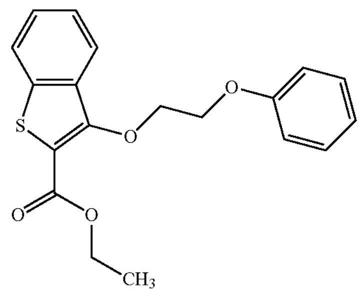 | $C_{19}H_{18}O_4S$ | 342.42 | M + 1 = 343 | 91.2 | 4.62 | 1.36 (t, 3H) 4.36 (m, 4H) 4.68 (t, 2H) 6.98 (m, 3H) 7.34 (m, 4H) 8.01 (m, 2H) |
| 20 | 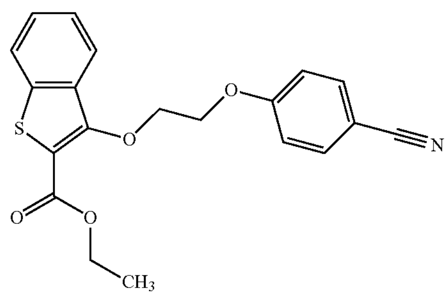 | $C_{20}H_{17}NO_4S$ | 367.43 | | 91.5 | 3.19 | 1.32 (t, 3H) 4.33 (q, 2H) 4.47 (t, 2H) 4.68 (t, 2H) 7.11 (m, 2H) 7.81 (m, 6H) |
| 21 | 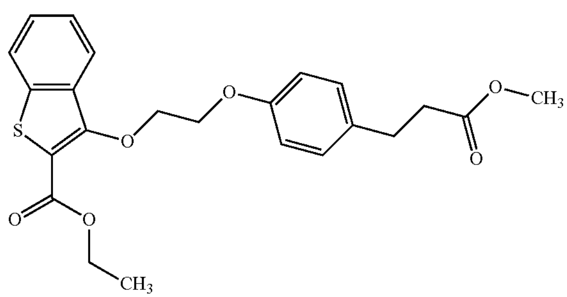 | $C_{23}H_{24}O_6S$ | 428.51 | M + 1 = 429 | 94.9 | 4.46 | 1.14 (t, 3H) 2.42 (t, 2H) 2.62 (t, 2H) 4.12 (q, 2H) 4.46 (t, 2H) 6.88 (q, 4H) 7.40 (m, 2H) 7.79 (m, 2H) |

TABLE A-continued

Hewlett Packard LC/MSD (Simple Quad)- Orthogonal Spray - Source APCI, HP Series 1100 line with diode array.

| Products | Structure | Formula | Molecular weight (g.mol$^{-1}$) | MS | Purity (%) | Tr (Min) | 1H NMR 200 MHz DMSOd6 (δ ppm) |
|---|---|---|---|---|---|---|---|
| 22 | 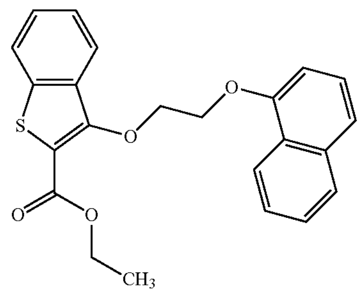 | $C_{23}H_{20}O_4S$ | 392.48 | M + 1 = 393 | 80 | 5.5 | 1.50 (t, 3H) 4.52 (q, 2H) 4.76 (m, 2H) 5.06 (m, 2H) 7.23 (m, 1H) 7.67 (m, 5H) 8.17 (m, 5H) |
| 23 | 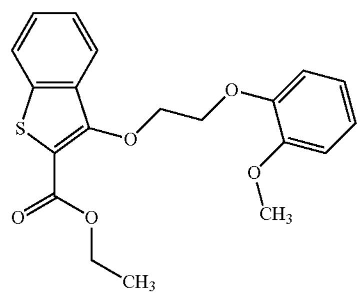 | $C_{20}H_{20}O_5S$ | 372.44 | M + 1 = 373 | 96.6 | 3.66 | 1.19 (t, 3H) 3.63 (s, 3H) 4.17 (q, 2H) 4.50 (m, 2H) 6.84 (m, 4H) 7.44 (m, 2H) 7.87 (m, 2H) |
| 24 | 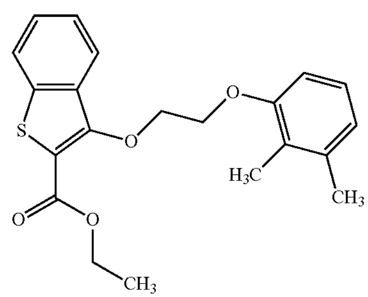 | $C_{21}H_{22}O_4S$ | 370.47 | M + 1 = 371 | 59 | 3.66 | 1.56 (t, 3H) 2.12 (s, 3H) 2.77 (s, 3H) 4.57 (m, 4H) 4.94 (m, 2H) 7.03 (m, 2H) 7.28 (t, 1H) 7.82 (m, 2H) 8.21 (m, 2H) |

TABLE A-continued

Hewlett Packard LC/MSD (Simple Quad)- Orthogonal Spray - Source APCI, HP Series 1100 line with diode array.

| Products | Structure | Formula | Molecular weight (g.mol$^{-1}$) | MS | Purity (%) | Tr (Min) | 1H NMR 200 MHz DMSOd6 (δ ppm) |
|---|---|---|---|---|---|---|---|
| 25 | 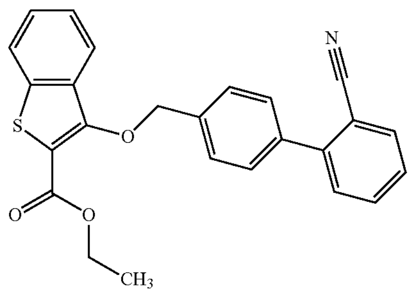 | $C_{25}H_{19}NO_3S$ | 413.50 | M + 1 = 414 | 77.4 | 4.94 | 1.37 (t, 3H) 4.38 (q, 2H) 5.46 (s, 2H) 7.69 (m, 12H) |
| 26 | 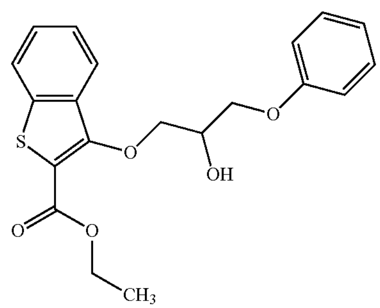 | $C_{20}H_{20}O_5S$ | 372.44 | M + 1 = 373 | 88.7 | 3.68 | 1.15 (t, 3H) 3.94 (m, 2H) 4.16 (m, 4H) 5.25 (d, 1H) 6.80 (m, 3H) 7.12 (m, 2H) 7.40 (m, 2H) 7.79 (m, 2H) |
| 27 | 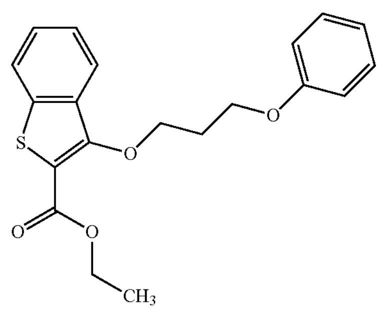 | $C_{20}H_{20}O_4S$ | 356.44 | M + 1 = 357 | 84.9 | 6.49 | 1.45 (t, 3H) 2.38 (t, 2H) 4.37 (m, 4H) 4.59 (t, 2H) 7.07 (m, 3H) 7.43 (m, 4H) 8.09 (m, 2H) |

TABLE A-continued

Hewlett Packard LC/MSD (Simple Quad)- Orthogonal Spray - Source APCI, HP Series 1100 line with diode array.

| Products | Structure | Formula | Molecular weight (g.mol$^{-1}$) | MS | Purity (%) | Tr (Min) | 1H NMR 200 MHz DMSOd6 (δ ppm) |
|---|---|---|---|---|---|---|---|
| 28 | 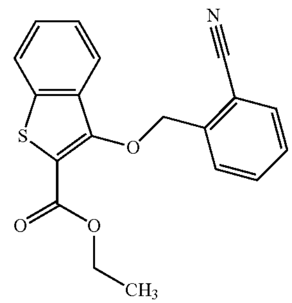 | $C_{19}H_{15}NO_3S$ | 337.40 | M + 1 = 338 | 94.8 | 3.22 | |
| 29 | 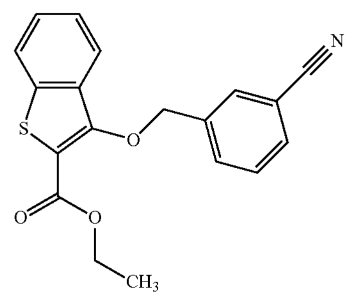 | $C_{19}H_{15}NO_3S$ | 337.40 | M + 1 = 338 | 37.4 | 2.24 | 1.34 (t, 3H) 4.66 (q, 2H) 5.43 (s, 2H) 7.67 (m, 3H) 8.02 (m, 5H) |
| 30 | 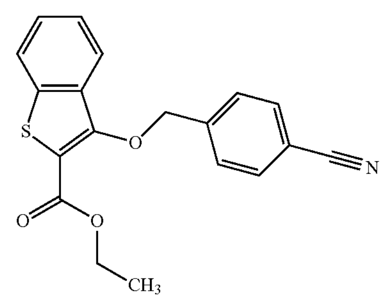 | $C_{19}H_{15}NO_3S$ | 337.40 | M + 1 = 338 | 94.3 | 3.45 | 1.33 (t, 3H) 4.39 (q, 2H) 5.48 (s, 2H) 7.59 (m, 3H) 7.92 (m, 5H) |

TABLE A-continued

Hewlett Packard LC/MSD (Simple Quad)- Orthogonal Spray - Source APCI, HP Series 1100 line with diode array.

| Products | Structure | Formula | Molecular weight (g.mol$^{-1}$) | MS | Purity (%) | Tr (Min) | 1H NMR 200 MHz DMSOd6 (δ ppm) |
|---|---|---|---|---|---|---|---|
| 31 | [structure: ethyl 3-((2-((phenylsulfonyl)methyl)benzyl)oxy)benzo[b]thiophene-2-carboxylate] | C$_{25}$H$_{22}$O$_5$S$_2$ | 466.58 | M + 1 = 467 | 99 | 3.48 | 1.49 (t, 3H) 4.51 (q, 2H) 5.10 (s, 2H) 5.51 (s, 2H) 7.88 (m, 12H) |
| 32 | [structure: ethyl 3-((4-(methoxycarbonyl)benzyl)oxy)benzo[b]thiophene-2-carboxylate] | C$_{20}$H$_{18}$O$_5$S | 370.43 | M + 1 = 371 | 92.4 | 4.83 | 1.29 (t, 3H) 3.86 (s, 3H) 4.34 (q, 2H) 5.42 (s, 2H) 7.66 (m, 5H) 8.01 (m, 3H) |

TABLE A-continued

Hewlett Packard LC/MSD (Simple Quad)- Orthogonal Spray - Source APCI, HP Series 1100 line with diode array.

| Products | Structure | Formula | Molecular weight (g.mol$^{-1}$) | MS | Purity (%) | Tr (Min) | 1H NMR 200 MHz DMSOd6 (δ ppm) |
|---|---|---|---|---|---|---|---|
| 33 | 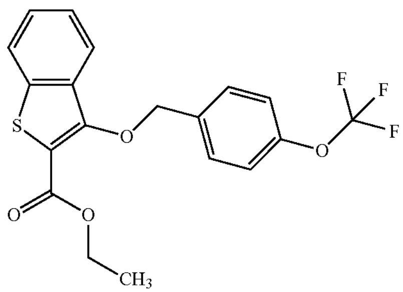 | $C_{19}H_{15}F_3O_4S$ | 396.39 | M + 1 = 397 | 49.9 | 6.93 | |
| 34 | 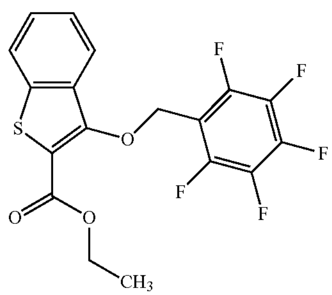 | $C_{18}H_{11}F_5O_3S$ | 402.34 | M + 1 = 403 | 98.9 | 6.34 | 1.15 (m, 3H) 4.18 (m, 2H) 5.31 (s, 2H) 7.54 (m, 4H) |
| 35 | 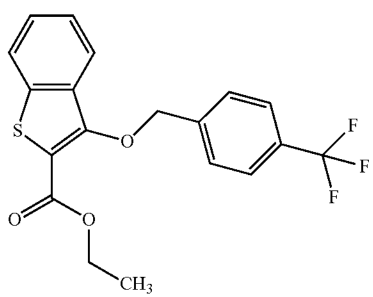 | $C_{19}H_{15}F_3O_3S$ | 380.39 | M + 1 = 381 | 79.6 | 6.49 | |

TABLE A-continued

Hewlett Packard LC/MSD (Simple Quad)- Orthogonal Spray - Source APCI, HP Series 1100 line with diode array.

| Products | Structure | Formula | Molecular weight (g.mol⁻¹) | MS | Purity (%) | Tr (Min) | 1H NMR 200 MHz DMSOd6 (δ ppm) |
|---|---|---|---|---|---|---|---|
| 36 | 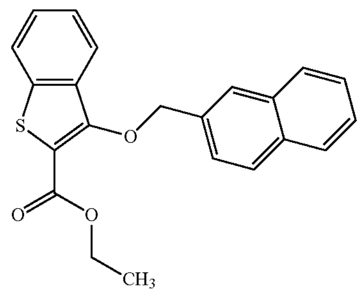 | $C_{22}H_{18}O_3S$ | 362.45 | M + 1 = 363 | 92.3 | 8.09 | |
| 37 | 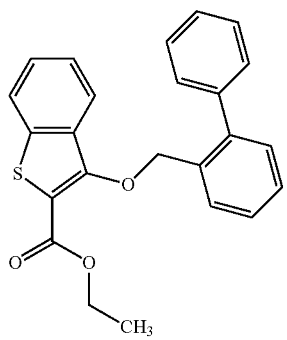 | $C_{24}H_{20}O_3S$ | 388.49 | M + 1 = 389 | 74.5 | 2.56 | |
| 38 | 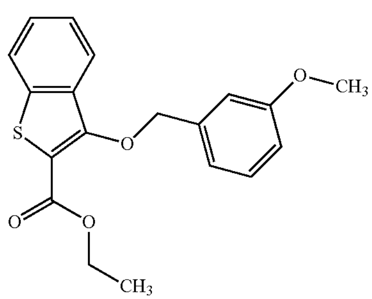 | $C_{19}H_{18}O_4S$ | 342.42 | M + 1 = 343 | 85.2 | 4.64 | 1.28 (t, 3H) 3.71 (s, 3H) 4.29 (q, 2H) 5.28 (s, 2H) 7.06 (m, 3H) 7.27 (m, 3H) 7.92 (m, 2H) |

TABLE A-continued

Hewlett Packard LC/MSD (Simple Quad)- Orthogonal Spray - Source APCL, HP Series 1100 line with diode array.

| Products | Structure | Formula | Molecular weight (g.mol$^{-1}$) | MS | Purity (%) | Tr (Min) | 1H NMR 200 MHz DMSOd6 (δ ppm) |
|---|---|---|---|---|---|---|---|
| 39 | (4-fluorobenzyloxy benzothiophene ethyl ester) | $C_{18}H_{15}FO_3S$ | 330.38 | M + 1 = 331 | 85.2 | 4.68 | 1.48 (t, 3H) 4.69 (q, 2H) 5.48 (s, 2H) 7.39 (m, 2H) 7.73 (m, 4H) 7.98 (m, 2H) |
| 40 | (4-bromobenzyloxy benzothiophene ethyl ester) | $C_{18}H_{15}BrO_3S$ | 391.29 | | 89.8 | 3.59 | 1.42 (t, 3H) 4.43 (q, 2H) 5.43 (s, 2H) 7.63 (m, 8H) |
| 41 | (4-methylbenzyloxy benzothiophene ethyl ester) | $C_{19}H_{18}O_3S$ | 326.42 | M + 1 = 327 | 79.7 | 6.21 | 1.36 (t, 3H) 2.34 (s, 2H) 4.40 (q, 2H) 5.33 (s, 2H) 7.41 (m, 8H) |

TABLE A-continued

Hewlett Packard LC/MSD (Simple Quad)- Orthogonal Spray - Source APCI, HP Series 1100 line with diode array.

| Products | Structure | Formula | Molecular weight (g.mol$^{-1}$) | MS | Purity (%) | Tr (Min) | 1H NMR 200 MHz DMSOd6 (δ ppm) |
|---|---|---|---|---|---|---|---|
| 42 | 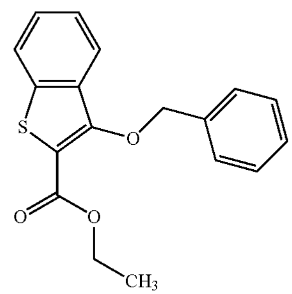 | $C_{18}H_{16}O_3S$ | 312.39 | M + 1 = 313 | 67.3 | 4.8 | |
| 43 | 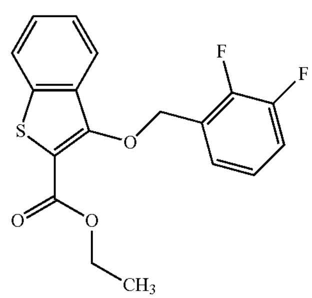 | $C_{18}H_{14}F_2O_3S$ | 348.37 | | | | 1.28 (t, 3H) 4.26 (q, 2H) 5.36 (s, 2H) 7.28 (m, 5H) 7.69 (m, 2H) |

By way of example, the following compounds were prepared according to the procedures described above:

4-(2-dimethylcarbamoylbenzo[b]thiophen-3-yloxy)butyric acid
5-(2-dimethylcarbamoylbenzo[b]thiophen-3-yloxy)pentanoic acid
6-(2-dimethylcarbamoylbenzo[b]thiophen-3-yloxy)hexanoic acid
3-{4-[2-(2-dimethylcarbamoylbenzo[b]thiophen-3-yloxy)ethoxy]phenyl}propionic acid
2-(2-dimethylcarbamoylbenzo[b]thiophen-3-yloxy)-4-phenylbutyric acid
2-(2-dimethylcarbamoylbenzo[b]thiophen-3-yloxy)pentanoic acid
{4-[2-(2-dimethylcarbamoylbenzo[b]thiophen-3-yloxy)ethoxy]phenyl}acetic acid
4-[2-(2-dimethylcarbamoylbenzo[b]thiophen-3-yloxy)ethoxy]benzoic acid
3-(2-dimethylcarbamoylbenzo[b]thiophen-3-yloxymethyl)benzoic acid
4-(2-dimethylcarbamoylbenzo[b]thiophen-3-yloxymethyl)benzoic acid
[2-(cyclohexylmethylcarbamoyl)benzo[b]thiophen-3-yloxy]acetic acid
4-[2-(cyclohexylmethylcarbamoyl)benzo[b]thiophen-3-yloxy]butyric acid
4-[2-(2,6-difluorophenylcarbamoyl)benzo[b]thiophen-3-yloxy]butyric acid
5-[2-(cyclohexylmethylcarbamoyl)benzo[b]thiophen-3-yloxy]pentanoic acid
5-[2-(2,6-difluorophenylcarbamoyl)benzo[b]thiophen-3-yloxy]pentanoic acid
6-[2-(cyclohexylmethylcarbamoyl)benzo[b]thiophen-3-yloxy]hexanoic acid
6-[2-(2,6-difluorophenylcarbamoyl)benzo[b]thiophen-3-yloxy]hexanoic acid
2-[2-(cyclohexylmethylcarbamoyl)benzo[b]thiophen-3-yloxy]-3-methoxypropionic acid
2-[2-(2,6-difluorophenylcarbamoyl)benzo[b]thiophen-3-yloxy]-3-methoxypropionic acid
3-(4-{2-[2-(cyclohexylmethylcarbamoyl)benzo[b]thiophen-3-yloxy]ethoxy}phenyl)propionic acid
3-(4-{2-[2-(2,6-difluorophenylcarbamoyl)benzo[b]thiophen-3-yloxy]ethoxy}phenyl)propionic acid
2-[2-(cyclohexylmethylcarbamoyl)benzo[b]thiophen-3-yloxy]butyric acid
2-[2-(2,6-difluorophenylcarbamoyl)benzo[b]thiophen-3-yloxy]butyric acid
2-[2-(cyclohexylmethylcarbamoyl)benzo[b]thiophen-3-yloxy]pentanoic acid
2-[2-(2,6-difluorophenylcarbamoyl)benzo[b]thiophen-3-yloxy]pentanoic acid
4-{2-[2-(cyclohexylmethylcarbamoyl)benzo[b]thiophen-3-yloxy]acetyl}benzoic acid
5-[2-(cyclohexylmethylcarbamoyl)benzo[b]thiophen-3-yloxy]-4-oxopentanoic acid
(4-{2-[2-(cyclohexylmethylcarbamoyl)benzo[b]thiophen-3-yloxy]ethoxy}phenyl)acetic acid
(4-{2-[2-(2,6-difluorophenylcarbamoyl)benzo[b]thiophen-3-yloxy]ethoxy}phenyl)acetic acid
4-[2-(cyclohexylmethylcarbamoyl)benzo[b]thiophen-3-yloxymethyl]benzoic acid II.—Biological Results Insulin Secretion Test According to the Method Described in *Endocrinology*, 1992 vol. 130 (1) pp. 167-178

The compounds according to the invention were tested at $10^{-5}$ M.

The insulin-secreting activities are collated in Table B.

TABLE B

| Products | SEC INS1 |
|---|---|
| 3 | 320% |
| 7 | 257% |
| 8 | 252% |
| 10 | 225% |
| 11 | 258% |
| 12 | 230% |
| 13 | 240% |
| 29 | 249% |

Study of the Activity on Isolated Rat Islets

Effect of the chemical compounds on insulin secretion as a function of the glucose concentration, in vitro, in isolated islets of Langerhans in static incubation (Table C):

The islets of Langerhans obtained by digestion of exocrine pancreatic tissue with collagenase, and then purified on Ficoll gradient, are incubated for 90 minutes in the presence of two concentrations of glucose, (2.8 mM or 8 mM), in the presence or absence of the chemical compound. The insulin secretion is assayed by RIA in the incubation medium.

The potential of the various chemical compounds to stimulate insulin secretion is estimated by calculating the stimulation factor*.

A compound stimulates the secretion of insulin if this factor is greater than or equal to 130% for a given dose of glucose.

$$^*\text{NB: Stimulation factor} = \frac{(G + \text{product}) * 100}{G}$$

where:

G=secretion of insulin (pmol/min. islet) in the presence of glucose alone

G+product=secretion of insulin (pmol/min. islet) in the presence of the same concentration of glucose and of the test chemical compound.

TABLE C

| | | Insulin secretion stimulation factor. | |
|---|---|---|---|
| | | Insulin secretion stimulation factor | |
| Product | Dose | Product + G 2.8 mM | Product + G 8 mM |
| 12 | $10^{-6}$ M | 90% | 189% |
| | $10^{-5}$ M | 93% | 186% |

The compounds according to the invention are thus insulin-secretory in response to glucose. They thus make it possible to avoid the risk of hypoglycaemia; this is in contrast with common hypoglycaemiant compounds, the hypoglycaemiant effect of which is independent of the concentration of glucose in the body.

The invention claimed is:
1. A compound of formula (I)

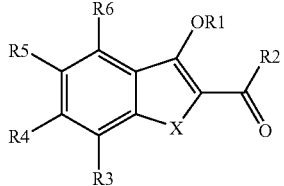

wherein
X is S;
R1 is
-Alk-COOH,
-Alk-C(=O)—(O)$_m$-Ar,
-Alk-C(=O)—(O)$_m$-Het,
-Alk-C(=O)—(O)$_m$-Alk,
-Alk-C(=O)—(O)$_m$-cycloalkyl,
-Alk-C(=O)NRR',
-Alk-(O)$_m$-Ar,
-Alk-O-Alk,
-Alk-O-Alk-Ar,
-Alk-O-Het;
R2 is —OH, —OAlk, —NR7R8, —OAr, —OHet or —O-cycloalkyl;
R7 is H or -Alk;
R8 is
—H;
-Alk' or -cycloalkyl,
which Alk' or cycloalkyl is optionally substituted by one or more of —OAlk, —CN, —OHet, —OH, —C(=O)—(O)$_m$Alk, —C(=O)—(O)$_m$Ar, —C(=O)—(O)$_m$Het, —C(=O)—(O)$_m$-cycloalkyl, —COOH or —NO$_2$;
—Ar' or Het',
which Ar' or Het' is optionally substituted by one or more of Hal, —OAlk, —OH, -Alk, —Ar, —OAlkAr, —OH, —CN, —OAr, —CF$_3$, -AlkAr, —COOH—NRR', -Het, —C(=O)—(O)$_m$Alk, —C(=O)—(O)$_m$Ar, —C(=O)—(O)$_m$Het, —C(=O)—(O)$_m$-cycloalkyl or NO$_2$;
or R7 and R8 form, together with the nitrogen atom to which they are attached, a nitrogenous heterocycle of 5 to 10 atoms;
R3, R4, R5 and R6, which may be identical or different, are each independently, H, -Hal, —OH, -Alk, —OAlk, —CN, —CF$_3$, —NRR' or —NO$_2$;
Alk, which may be identical or different, is optionally and independently substituted by one or more of -Hal, —OAlk, —Ar, —OAlkAr, —OH, —CN, —OAr, —CF$_3$, —COOH, —NRR', —C(=O)—(O)$_m$Alk, -Het or —NO$_2$;
Ar, each of which may be identical or different, is optionally and independently substituted by one or more of -Hal, —OAlk, -Alk, —Ar, —OAlkAr, —OH, —CN, —OAr, —CF$_3$, -AlkAr, —COOH, —C(=O)—(O)$_m$Alk, -Alk—C(=O)—(O)$_m$Alk, —NRR', -Het, —NO$_2$, —S(O)$_n$-Ar or —S(O)$_n$Alk;
R and R' are, each independently H or Alk;
is 0 or 1;
is 0, 1 or 2;
Alk and Alk' are, each independently, an alkyl radical;
Ar and Ar' are, each independently, an aryl radical;

Het and Het' are, each independently, a heteroarsrl radical; and
Hal is a halogen radical;
or pharmaceutically acceptable salt thereof,
with the exception of the compounds for which:
1) R1=CH$_2$-phenyl, optionally substituted by —NO$_2$ or —OMe, R2=—OMe, —OEt or —OH, R3, and R6=H, R4, and R5=H or —OMe, and X=S;
2) R1=—CH$_2$—C(=O)Me, R3, R4, R5, and R6=H, X=S, and R2=—OMe;
3) R1=—CH$_2$—CO$_2$Me, R3, R4, R5, and R6=H, R2=—OMe or —OH, and X=S;
and
R1=—CH$_2$CO$_2$H, R3, R4, R5, and R6=H, R2=OH, and X=S;
and
4) R1=—CH$_2$-phenyl, R2=—NH$_2$, X=S, and R5=—OMe.

2. A compound of according to claim 1, wherein
R2=—Oet;
R1 is
-Alk-COOH,
-Alk-C(=O)—(O)$_m$-Ar,
-Alk-C(=O)—(O)$_m$-Het,
-Alk-C(=O)—(O)$_m$-Alk,
-Alk-C(=O)—(O)$_m$-cycloalkyl,
-Alk-C(=O)NRR',
-Alk-(O)$_m$-Ar,
-Alk-O-Alk,
-Alk-O-Alk-Ar, or
-Alk-O-Het;
R3, R4, R5 and R6, which may be identical or different, are each independently, H, -Hal, —OH, -Alk, —OAlk, —CN, —CF$_3$, —NRR' or —NO$_2$;
Alk, each of which may be identical or different, is optionally and independently substituted by one or more of -Hal, —OAlk, —Ar, —OAlkAr, —OH, —CN, —OAr, —CF$_3$, —COOH, —NRR', —C(=O)—(O)$_m$Alk, -Het or —NO$_2$;
Ar, each which may be identical or different, is optionally and independently substituted by one or more of -Hal, —OAlk, -Alk, —Ar, —OAlkAr, —OH, —CN, —OAr, —CF$_3$, -AlkAr, —COOH, —C(=O)—(O)$_m$Alk, -Alk-C(=O)—(O)$_m$Alk, —NRR', -Het, —NO$_2$, —S(O)$_n$-Ar or —S(O)$_n$Alk;
R and R' are, each independently H or Alk;
m is 0 or 1;
n is 0, 1 or 2.

3. A compound according to claim 1, in which
R1 is
-Alk-COOH,
-Alk-C(=O)—(O)$_m$-Ar,
-Alk-C(=O)—(O)$_m$-Het,
-Alk-C(=O)—(O)$_m$-Alk,
-Alk-C(=O)—(O)$_m$-cycloalkyl,
-Alk-C(=O)NRR',
-Alk-(O)$_m$-Ar,
-Alk-O-Alk,
-Alk-O-Alk-Ar,
-Alk-O-Het;
R2 is —NR7R8 in which
R7 is H or -Alk;
R8 is
-Alk' or -cycloalkyl,
which Alk' or cycloalkyl is optionally substituted by one or more of —OAlk, —CN, —OHet, —OH, —C(=O)—(O)$_m$Alk,    —C(=O)—(O)$_m$Ar,
—C(=O)—(O)$_m$Het,    —C(=O)—(O)$_m$cycloalkyl,
—COOH and —NO$_2$;
—Ar' or Het';
which Ar' or Het' is optionally substituted by one or more Hal, —OAlk, —OH, -Alk, —Ar, —OAlkAr, —OH, —CN, —OAr, —CF$_3$, -AlkAr, —COOH—NRR', -Het, —C(=O)—(O)$_m$Alk,    —C(=O)—(O)$_m$Ar, —C(=O)—(O)$_m$Het, —C(=O)—(O)$_m$cycloalkyl or NO$_2$;
R3, R4, R5 and R6, which may be identical or different, are each independently, H, -Hal, —OH, -Alk, —OAlk, —CN, —CF$_3$, —NRR' or —NO$_2$;
Alk, each of which may be identical or different, is optionally and independently substituted by one or more -Hal, —OAlk, —Ar, —OAlkAr, —OH, —CN, —OAr, —CF$_3$, —COOH, —NRR', —C(=O)—(O)$_m$Alk, -Het or —NO$_2$;
Ar, which may be identical or different, is optionally and independently substituted by one or more of -Hal, —OAlk, -Alk, —Ar, —OAlkAr, —OH, —CN, —OAr, —CF$_3$, -AlkAr, —COOH, —C(=O)—(O)$_m$Alk, -Alk-C(=O)—(O)$_m$Alk, —NRR', -Het, NO$_2$, —S(O)$_n$-Ar or —S(O)$_n$Alk;
R and R' are, each independently H or Alk;
m is 0 or 1;
n is 0, 1 or 2.

4. A compound according to claim 1, in which R3, R4, R5 and R6 are H.

5. A compound according to claim 1, in which R2 is —OAlk.

6. A compound according to claim 1, in which m is 0.

7. A compound according to claim 1, in which R2 is —NR7R8,
R7 is H or Alk, and
R8 is —Alk' optionally substituted by —C(=O)—OAlk, -Het' or, —Ar' optionally substituted by -Hal, —C(=O)OAlk or -Alk-C(=O)OAlk.

8. A compound according to claim 1, in which
R1 is —CH$_2$—COOH, —CH$_2$—C(=O)—(O)$_m$-Ar, —CH$_2$—C(=O)—(O)$_m$-Het, —CH$_2$—C(=O)—(O)$_m$-Alk, —CH$_2$—C(=O)NRR', —CH$_2$—(O)$_m$-Ar, —CH$_2$—O-Alk, —CH$_2$—O-Alk-Ar or —CH$_2$—O-Het;
Ar is optionally substituted by one or more of Hal, —OAlk, —Ar, -Alk, —O-Alk-Ar, —C(=O)—(O)$_m$-Alk, -Alk-C(=O)—(O)$_m$Alk, —S(O)$_n$-Ar, —S(O)$_n$-Alk, —O—CF$_3$, —CN or —OH,
m is 0, and n is 2.

9. A compound according to claim 1, in which R1 is —CH$_2$—C(=O)—Ar, —CH$_2$—C(=O)-Alk or —(CH$_2$)—(CH$_2$)$_m$'—(O)$_m$-Ar,
Ar is optionally substituted by one or more of Hal, —OAlk, —Ar, -Alk, —O-Alk-Ar, —C(=O)—(O)$_m$-Alk, -Alk-C(=O)—(O)$_m$Alk, —S(O)$_n$-Ar, —S(O)$_n$-Alk, —O—CF$_3$, —CN or —OH,
m is 0 or 1, m' is 1 or 2, n is 2.

10. A compound according to claim 9, in which m' is 2 and m is 1.

11. A compound according to claim 1, in which Ar is phenyl.

12. A compound according to claim 1, in which R1 is —CH$_2$—C(=O)Alk.

13. A compound according to claim 12, in which Alk is —CMe$_3$.

14. A compound according to claim 1, in which R1 is —CH$_2$—C(=O)-phenyl or —CH$_2$-phenyl, in which phenyl is optionally substituted by one or more of -Hal, —OAlk or —CN.

15. A compound according to claim 1, which is
ethyl 3-[2-(4-chlorophenyl)-2-oxoethoxy]benzo[b]thiophene-2-carboxylate;
ethyl 3-(2-oxo-2-phenylethoxy)benzo[b]thiophene-2-carboxylate;
ethyl 3-[2-(2-methoxyphenyl)-2-oxoethoxy]benzo[b]thiophene-2-carboxylate;
ethyl 3-(2-biphenyl-4-yl-2-oxoethoxy)benzo[b]thiophene-2-carboxylate;
ethyl 3-(2-oxo-2-p-tolylethoxy)benzo[b]thiophene-2-carboxylate;
ethyl 3-(2-adamantan-1-yl-2-oxoethoxy)benzo[b]thiophene-2-carboxylate;
ethyl 3-[2-(4-fluorophenyl)-2-oxoethoxy]benzo[b]thiophene-2-carboxylate;
ethyl 3-[2-(3-methoxyphenyl)-2-oxoethoxy]benzo[b]thiophene-2-carboxylate;
ethyl 3-[2-(4-benzyloxyphenyl)-2-oxoethoxy]benzo[b]thiophene-2-carboxylate;
ethyl 3-(1-methyl-2-oxo-2-phenylethoxy)benzo[b]thiophene-2-carboxylate;
ethyl 3-[2-(2,4-dimethoxyphenyl)-2-oxoethoxy]benzo[b]thiophene-2-carboxylate;
ethyl 3-(3,3-dimethyl-2-oxobutoxy)benzo[b]thiophene-2-carboxylate;
ethyl 3-(2-naphthalen-2-yl-2-oxoethoxy)benzo[b]thiophene-2-carboxylate;
ethyl 3-[2-(2,3-dichloro-4-methoxyphenyl)-2-oxoethoxy]benzo[b]thiophene-2-carboxylate;
ethyl 3-[2-(2-benzyloxy-5-fluorophenyl)-2-oxoethoxy]benzo[b]thiophene-2-carboxylate;
ethyl 3-hydroxybenzo[b]thiophene-2-carboxylate;
ethyl 3-[2-(4-fluorophenoxy)ethoxy]benzo[b]thiophene-2-carboxylate;
ethyl 3-phenethyloxybenzo[b]thiophene-2-carboxylate;
ethyl 3-(2-phenoxyethoxy)benzo[b]thiophene-2-carboxylate;
ethyl 3-[2-(4-cyanophenoxy)ethoxy]benzo[b]thiophene-2-carboxylate;
ethyl 3-{2-[4-(2-methoxycarbonylethyl)phenoxy]ethoxy}benzo[b]thiophene-2-carboxylate;
ethyl 3-[2-(naphthalen-1-yloxy)ethoxy]benzo[b]thiophene-2-carboxylate;
ethyl 3-[2-(2-methoxyphenoxy)ethoxy]benzo[b]thiophene-2-carboxylate;
ethyl 3-[2-(2,3-dimethylphenoxy)ethoxy]benzo[b]thiophene-2-carboxylate;
ethyl 3-(2'-cyanobiphenyl-4-ylmethoxy)benzo[b]thiophene-2-carboxylate;
ethyl 3-(2-hydroxy-3-phenoxypropoxy)benzo[b]thiophene-2-carboxylate;
ethyl 3-(3-phenoxypropoxy)benzo[b]thiophene-2-carboxylate;
ethyl 3-(2-cyanobenzyloxy)benzo[b]thiophene-2-carboxylate;
ethyl 3-(3-cyanobenzyloxy)benzo[b]thiophene-2-carboxylate;
ethyl 3-(4-cyanobenzyloxy)benzo[b]thiophene-2-carboxylate;
ethyl 3-(2-benzenesulfonylmethylbenzyloxy)benzo[b]thiophene-2-carboxylate;
ethyl 3-(4-methoxycarbonylbenzyloxy)benzo[b]thiophene-2-carboxylate;

ethyl 3-(4-trifluoromethoxybenzyloxy)benzo[b]thiophene-2-carboxylate;
ethyl 3-pentafluorophenylmethoxybenzo[b]thiophene-2-carboxylate;
ethyl 3-(4-trifluoromethylbenzyloxy)benzo[b]thiophene-2-carboxylate;
ethyl 3-(naphthalen-2-ylmethoxy)benzo[b]thiophene-2-carboxylate;
ethyl 3-(biphenyl-2-ylmethoxy)benzo[b]thiophene-2-carboxylate;
ethyl 3-(3-methoxybenzyloxy)benzo[b]thiophene-2-carboxylate;
ethyl 3-(4-fluorobenzyloxy)benzo[b]thiophene-2-carboxylate;
ethyl 3-(4-bromobenzyloxy)benzo[b]thiophene-2-carboxylate;
ethyl 3-(4-methylbenzyloxy)benzo[b]thiophene-2-carboxylate;
ethyl 3-benzyloxybenzo[b]thiophene-2-carboxylate;
ethyl 3-(2,3-difluorobenzyloxy)benzo[b]thiophene-2-carboxylate;
or a pharmaceutically acceptable salt thereof.

16. A process for preparing of a compound according to claim 1, comprising reacting
a compound of formula (IV)

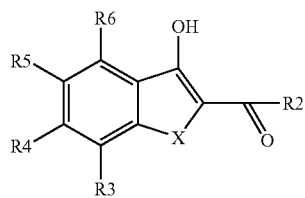
(IV)

with a compound formula (V)

Hal-R1    (V)

R1-R6 are defined as for the compounds of formula (I), in a polar solvent, at a temperature of −20 to 200° C.

17. A process for preparing a compound according to claim 1, comprising reacting a compound of formula (II)

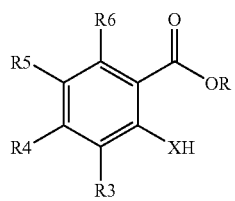
(II)

wherein R3-R6 and X are as defined in for the compounds of formula (I), and
R represents a hydrogen atom or an alkyl radical, with a compound of formula (III)

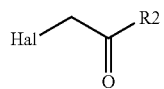
(III)

wherein Hal represents a halogen atom and R2 is as defined for the compounds of formula (I), in a polar solvent, at a temperature of −20 to 200° C., followed by cyclization in a polar solvent, at a temperature of −20 to 200° C.

18. A process according to claim 17, wherein the polar solvent is ethanol, methanol, water, DMF, NMP, DMSO or iPrOH.

19. A pharmaceutical compositions comprising a pharmaceutically acceptable carrier and a compound of formula (I)

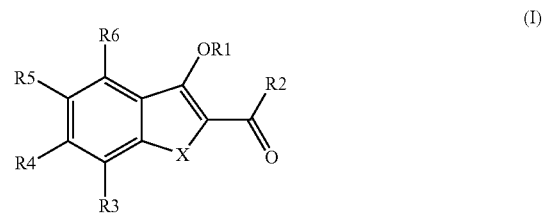
(I)

in which:
X is S;
R1 is
-Alk-COOH,
-Alk-C(=O)—(O)$_m$-Ar,
-Alk-C(=O)—(O)$_m$-Het,
-Alk-C(=O)—(O)$_m$-Alk,
-Alk-C(=O)—(O)$_m$-cycloalkyl,
-Alk-C(=O)NRR',
-Alk-(O)$_m$-Ar,
-Alk-O-Alk,
-Alk-O-Alk-Ar,
-Alk-O-Het;
R2 is —OH, —OAlk, —NR7R8, —OAr, —OHet or —O-cycloalkyl;
R7 is H or -Alk;
R8 is
—H;
-Alk' or -cycloalkyl,
which Alk' or cycloalkyl is optionally substituted by one or more of —OAlk, —CN, —OHet, —OH, —C(=O)—(O)$_m$Alk, —C(=O)—(O)$_m$Ar, —C(=O)—(O)$_m$Het, —C(=O)—(O)$_m$-cycloalkyl, —COOH or —NO$_2$;
—Ar' or Het',
which Ar' or Het' is optionally substituted by one or more Hal, —OAlk, —OH, -Alk, —Ar, —OAlkAr, —OH, —CN, —OAr, —CF$_3$, —AlkAr, —COOH—NRR', -Het, —C(=O)—(O)$_m$Alk, —C(=O)—(O)$_m$Ar, —C(=O)—(O)$_m$Het, —C(=O)—(O)$_m$-cycloalkyl and NO$_2$;
or R7 and R8 form, together with the nitrogen atom to which they are attached, a nitrogenous heterocycle of 5 to 10 atoms;
R3, R4, R5 and R6, which may be identical or different, are each independently, H, -Hal, —OH, -Alk, —OAlk, —CN, —CF$_3$, —NRR' or —NO$_2$;
Alk, each of which may be identical or different, is optionally and independently substituted by one or more of -Hal, —OAlk, —Ar, —OAlkAr, —OH, —CN, —OAr, —CF$_3$, —COOH, —NRR', —C(=O)—(O)$_m$Alk, -Het or —NO$_2$;
Ar, each of which may be identical or different, is optionally and independently substituted by one or more of -Hal, —OAlk, -Alk, —Ar, —OAlkAr, —OH, —CN, —OAr, —CF$_3$, -AlkAr, —COOH, —C(=O)—(O)$_m$Alk, -Alk-C(=O)—(O)$_m$Alk, —NRR', -Het, —NO$_2$, S(O)$_n$-Ar or —S(O)$_n$Alk;

R and R' are independently H or Alk;

m is 0 or 1;

n is 0, 1 or 2;

Alk and Alk' are, each independently, an alkyl radical;

Ar and Ar' are, each independently, an aryl radical;

Het and Het' are, each independently, a heteroaryl radical; and

Hal is a halogen radical;

or a pharmaceutically acceptable salt thereof.

20. A pharmaceutical composition, comprising a pharmaceutically acceptable carrier and a compound of claim 2.

21. A method for reducing hyperglycaemia, comprising administering to a subject in need thereof an effective amount of a compound of formula (I)

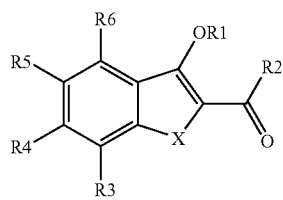

wherein

X is S;

R1 is

-Alk-COOH,

-Alk-C(=O)—(O)$_m$-Ar,

-Alk-C(=O)—(O)$_m$-Het,

-Alk-C(=O)—(O)$_m$-Alk,

-Alk-C(=O)—(O)$_m$-cycloalkyl,

-Alk-C(=O)NRR',

-Alk-(O)$_m$-Ar,

-Alk-O-Alk,

-Alk-O-Alk-Ar,

-Alk-O-Het;

R2 is —OH, —OAlk, —NR7R8, —OAr, —OHet or —O-cycloalkyl;

R7 is H or -Alk;

R8 is

—H;

-Alk' or -cycloalkyl, which Alk' or cycloalkyl is optionally substituted by one or more of —OAlk, —CN, —OHet, —OH, —C(=O)—(O)$_m$Alk, —C(=O)—(O)$_m$Ar, —C(=O)—(O)$_m$Het, —C(=O)—(O)$_m$-cycloalkyl, —COOH or —NO$_2$;

—Ar' or Het', which Ar' or Het' is optionally substituted by one or more of Hal, —OAlk, —OH, -Alk, —Ar, —OAlkAr, —OH, —CN, —OAr, —CF$_3$, -AlkAr, —COOH—NRR', -Het, —C(=O)—(O)$_m$Alk, —C(=O)—(O)$_m$Ar, —C(=O)—(O)$_m$Het, —C(=O)—(O)$_m$-cycloalkyl or NO$_2$;

or R7 and R8 form, together with the nitrogen atom to which they are attached, a nitrogenous heterocycle of 5 to 10 atoms;

R3, R4, R5 and R6, which may be identical or different, are each independently H, -Hal, —OH, -Alk, —OAlk, —CN, —CF$_3$, —NRR' or —NO$_2$;

Alk, each of which may be identical or different, is optionally and independently substituted by one or more of -Hal, —OAlk, —Ar, —OAlkAr, —OH, —CN, —OAr, —CF$_3$, —COOH, —NRR', —C(=O)—(O)$_m$Alk, -Het or —NO$_2$;

Ar, each of which may be identical or different, is optionally and independently substituted by one or more of -Hal, —OAlk, -Alk, —Ar, —OAlkAr, —OH, —CN, —OAr, —CF$_3$, -AlkAr, —COOH, —C(=O)—(O)$_m$Alk, -Alk-C(=O)—(O)$_m$Alk, —NRR', -Het, —NO$_2$, —S(O)$_n$-Ar or —S(O)$_n$Alk;

R and R' are, each independently, H or Alk;

m is 0 or 1;

n is 0, 1 or 2;

Alk and Alk' are, each independently, an alkyl radical;

Ar and Ar' are, each independently, an aryl radical;

Het and Het' are, each independently, a heteroaryl radical; and

Hal is a halogen radical;

or a pharmaceutically acceptable salt thereof.

22. A method according to claim 21, wherein diabetes is treated.

23. A method according to claim 21, wherein non-insulin-dependent diabetes is treated.

24. A method according to claim 21, wherein dyslipidaemia and/or obesity is treated.

25. A method according to claim 21, wherein diabetes-related microvascular or macrovascular complication is treated or prevented.

26. A method according to claim 25, wherein the microvascular or macrovascular complication is atherosclerosis, arterial hypertension, a diabetes-related inflammatory processes, microangiopathy, macroangiopathy, retinopathy or neuropathy.

27. A pharmaceutical composition, comprising a pharmaceutically acceptable carrier and a compound of claim 1.

28. A method for reducing hyperglycaemia, comprising administering to a subject in need thereof an effective amount of a compound of claim 1.

29. A compound of claim 1, wherein

R1 is

-Alk-COOH,

-Alk-C(=O)-(O)$_m$-Ar,

-Alk-C(=O)-(O)$_m$-Alk,

-Alk-C(=O)-(O)$_m$-cycloalkyl,

-Alk-C(=O)NRR',

-Alk-(O)$_m$-Ar,

-Alk-O-Alk, or

-Alk-O-Alk-Ar;

R2 is —OH, —OAlk, —NR7R8, —OAr, —OHet or —O-cycloalkyl;

R7 is H or -Alk;

R8 is

—H;

-Alk' or -cycloalkyl, which Alk' or cycloalkyl is optionally substituted by one or more of —OAlk, —CN, —OH, —C(=O)-(O)$_m$Alk, —C(=O)-(O)$_m$Ar, —C(=O)-(O)$_m$-cycloalkyl, —COOH or —NO$_2$;

—Ar', which Ar' is optionally substituted by one or more of Hal, —OAlk, —OH, -Alk, —Ar, —OAlkAr, —OH, —CN, —OAr, —CF$_3$, -AlkAr, —COOH —NRR', —C(=O)-(O)$_m$Alk, —C(=O)$_m$Ar, —C(=O)-(O)$_m$-cycloalkyl or NO$_2$;

R3, R4, R5 and R6, which may be identical or different, are each independently, H, -Hal, —OH, -Alk, —OAlk, —CN, —CF$_3$, —NRR' or —NO$_2$;

Alk, each of which may be identical or different, is optionally and independently substituted by one or more of -Hal, —OAlk, —Ar, —OAlkAr, —OH, —CN, —OAr, —CF$_3$, —COOH, —NRR', —C(=O)-(O)$_m$Alk, or —NO$_2$;

Ar, each of which may be identical or different, is optionally and independently substituted by one or more of -Hal, —OAlk, -Alk, —Ar, —OAlkAr, —OH, —CN, —OAr, —CF$_3$, -AlkAr, —COOH, —C(=O)-(O)$_m$Alk, -Alk-C(=O)-(O)$_m$Alk, —NRR', —NO$_2$, —S(O)$_n$-Ar or —S(O)$_n$Alk;

R and R' are, each independently, H or Alk;

m is 0 or 1;

n is 0, 1 or 2;

Alk and Alk' are, each independently, an alkyl radical;

Ar and Ar' are, each independently, an aryl radical; and

Hal is a halogen radical;

or a pharmaceutically acceptable salt thereof.

30. A pharmaceutical composition of claim 19, wherein

X is S;

R1 is -Alk-COOH,

-Alk-C(=O)-(O)$_m$-Ar,

-Alk-C(=O)-(O)$_m$-Alk,

-Alk-C(=O)-(O)$_m$-cycloalkyl,

-Alk-C(=O)NRR',

-Alk-(O)$_m$-Ar,

-Alk-O-Alk, or

-Alk-O-Alk-Ar;

R2 is —OH, —OAlk, —NR7R8, —OAr, or —O-cycloalkyl;

R7 is H or -Alk;

R8 is —H;

-Alk' or -cycloalkyl, which Alk' or cycloalkyl is optionally substituted by one or more of —OAlk, —CN, —OH, —C(=O)-(O)$_m$Alk, —C(=O)-(O)$_m$Ar, —C(=O)-(O)$_m$-cycloalkyl, —COOH or —NO$_2$; —Ar', which Ar' is optionally substituted by one or more of Hal, —OAlk, —OH, —Alk, —Ar, —OAlkAr, —OH, —CN, —OAr, —CF$_3$, -AlkAr, —COOH—NRR', —C(=O)-(O)$_m$Alk, —C(=O)-(O)$_m$Ar, —C(=O)-(O)$_m$-cycloalkyl or NO$_2$;

R3, R4, R5 and R6, which may be identical or different, are each independently, H, -Hal, —OH, -Alk, —OAlk, —CN, —CF$_3$, —NRR' or —NO$_2$;

Alk, each of which may be identical or different, is optionally and independently substituted by one or more of -Hal, —OAlk, —Ar, —OAlkAr, —OH, —CN, —OAr, —CF$_3$, —COOH, —NRR', —C(=O)-(O)$_m$Alk, or —NO$_2$;

Ar, each of which may be identical or different, is optionally and independently substituted by one or more of -Hal, —OAlk, -Alk, —Ar, —OAlkAr, —OH, —CN, —OAr, —CF$_3$, -AlkAr, —COOH, —C(=O)-(O)$_m$Alk, -Alk-C(=O)-(O)$_m$Alk, —NRR', —NO$_2$, —S(O)$_n$-Ar or —S(O)$_n$Alk;

R and R' are, each independently, H or Alk;

m is 0 or 1;

n is 0, 1 or 2;

Alk and Alk' are, each independently, an alkyl radical;

Ar and Ar' are, each independently, an aryl radical; and

Hal is a halogen radical;

or a pharmaceutically acceptable salt thereof.

31. A method according to claim 21, wherein

X is S;

R1 is

-Alk-COOH,

-Alk-C(=O)-(O)$_m$-Ar,

-Alk-C(=O)-(O)$_m$-Alk,

-Alk-C(=O)-(O)$_m$-cycloalkyl,

-Alk-C(=O)NRR',

-Alk-(O)$_m$-Ar,

-Alk-O-Alk, or

-Alk-O-Alk-Ar;

R2 is —OH, —OAlk, —NR7R8, —OAr, or —O-cycloalkyl;

R7 is H or -Alk;

R8 is —H;

-Alk' or -cycloalkyl, which Alk' or cycloalkyl is optionally substituted by one or more of —OAlk, —CN, —OH, —C(=O)-(O)$_m$Alk, —C(=O)-(O)$_m$Ar, —C(=O)-(O)$_m$-cycloalkyl, —COOH or —NO$_2$;

—Ar', which Ar' is optionally substituted by one or more of Hal, —OAlk, —OH, -Alk, —Ar, —OAlkAr, —OH, —CN, —OAr, —CF$_3$, -AlkAr, —COOH —NRR', —C(=O)-(O)$_m$Alk, C(=O)-(O)$_m$Ar, —C(=O)-(O)$_m$-cycloalkyl or NO$_2$;

R3, R4, R5 and R6, which may be identical or different, are each independently, H, -Hal, —OH, -Alk, —OAlk, —CN, —CF$_3$, —NRR' or —NO$_2$;

Alk, each of which may be identical or different, is optionally and independently substituted by one or more of -Hal, —OAlk, —Ar, —OAlkAr, —OH, —CN, —OAr, —CF3, —COOH, —NRR', —C(=O)-(O)$_m$ Alk, or —NO$_2$;

Ar, each of which may be identical or different, is optionally and independently substituted by one or more of -Hal, —OAlk, -Alk, —Ar, —OAlkAr, —OH, —CN, —OAr, —CF$_3$, -AlkAr, —COOH, C(=O)-(O)$_m$Alk, -Alk-C(=O)-(O)$_m$Alk, —NRR', —NO$_2$, —S(O)$_n$-Ar or —S(O)$_n$Alk;

R and R' are, each independently, H or Alk;

m is 0 or 1;

n is 0, 1 or 2;

Alk and Alk' are, each independently, an alkyl radical;

Ar and Ar' are, each independently, an aryl radical; and

Hal is a halogen radical;

or a pharmaceutically acceptable salt thereof.

* * * * *

UNITED STATES PATENT AND TRADEMARK OFFICE
CERTIFICATE OF CORRECTION

PATENT NO. : 7,375,130 B2  
APPLICATION NO. : 10/580033  
DATED : May 20, 2008  
INVENTOR(S) : Gerard Moinet It is certified that error appears in the above-identified patent and that said Letters Patent is hereby corrected as shown below:

Column 47, line 52 reads "Alk, which" should read --Alk, each of which--  
Column 47, line 64 reads "is 0" should read --m is.0--  
Column 47, line 65 reads "is 0" should read --n is 0--  
Column 48, line 1 reads "heteroarsrl" should read --heteroaryl--  
Column 49, line 19 reads "Ar, which" should read --Ar, each of which--  
Column 49, line 29 reads "R5and R6are H" should read --R5 and R6 are H--  
Column 49, line 37 reads "R8is" should read --R8 is--  
Column 49, line 41 reads "R1is" should read --R1 is--  
Column 49, line 50 reads "m is 0, and n is 2" should read --m is 0 or 1, and n is 2--  
Column 49, line 51 reads "R1is" should read --R1 is--  
Column 49, line 52 delete "–(CH$_2$)" at the end of line  
Column 49, line 64 reads "R1is" should read --R1 is--  
Column 50, line 1 reads "R1is" should read --R1 is--  
Column 51, line 19 reads "ethyl 3-benzyloxybenzo[b]thiophene-2-carboxylate;" should read --ethyl 3-benzyloxybenzo[b]thiophene-2-carboxylate; or--  
Column 51, line 40 reads "Hal-R1" should read --Hal-R1 (V)--  
Column 51, line 41 reads "R1-R6 are defined as" should read --R1-R6 and X are defined as--  
Column 51, line 56 reads "defines in for" should read --defines for--  
Column 52, line 9 reads "compositions" should read --composition--  
Column 52, line 32 reads "-Alk-O-Alk," should read -- -Alk-O-Alk, or--  
Column 52, line 33 reads "-Alk-O-Alk-Ar," should read -- -Alk-O-Alk-Ar, or--  
Column 52, line 53 reads "and NO$_2$" should read --or NO$_2$--  
Column 54, line 34 reads "processes" should read --process--  
Column 54, line 52 delete –OHet.  
Column 55, line 44 reads "–C(=0)-" should read -- –C(=O)--

Signed and Sealed this

Twenty-sixth Day of August, 2008

JON W. DUDAS  
*Director of the United States Patent and Trademark Office*